(12) United States Patent  
Strohmeyer et al.

(10) Patent No.: US 7,100,422 B2  
(45) Date of Patent: Sep. 5, 2006

(54) SYSTEMS AND METHODS FOR RESIDUE COLLECTION WITH IMPROVED LETTER HANDLING CAPABILITY

(75) Inventors: James J. Strohmeyer, Ballwin, MO (US); William Blumfelder, Florissant, MO (US); John Tehan, Chesterfield, MO (US); Dennis Osterhorn, St. Louis, MO (US); Joseph Matteoni, St. Charles, MO (US); William J. Nelgner, St. Charles, MO (US); Brian Lybarger, Granite, IL (US); David Schenken, St. Louis, MO (US); James Wagy, Olivette, MO (US)

(73) Assignee: DRS Sustainment Systems, Inc., St. Louis, MO (US)

( * ) Notice: Subject to any disclaimer, the term of this patent is extended or adjusted under 35 U.S.C. 154(b) by 0 days.

(21) Appl. No.: 10/941,273

(22) Filed: Sep. 15, 2004

(65) Prior Publication Data

US 2005/0076722 A1    Apr. 14, 2005

Related U.S. Application Data

(63) Continuation-in-part of application No. 10/449,612, filed on May 30, 2003, now Pat. No. 6,941,794.

(60) Provisional application No. 60/385,004, filed on May 31, 2002.

(51) Int. Cl.  
  *G01N 1/22* (2006.01)  
  *B07C 1/04* (2006.01)

(52) U.S. Cl. ............... 73/28.01; 73/863.71; 73/864.33

(58) Field of Classification Search ............... 73/23.2, 73/28.01, 31.02, 31.03, 31.04, 31.07, 863.21, 73/863.22, 863.23, 864.33; 340/540, 632; 435/287.1; 702/402, 410

See application file for complete search history.

(56) References Cited

U.S. PATENT DOCUMENTS

| 3,291,282 | A | * | 12/1966 | Pedagno | 198/550.4 |
| 3,998,101 | A | | 12/1976 | Bradshaw et al. | 73/864 |
| 4,111,049 | A | | 9/1978 | Lerner et al. | 73/864.73 |
| 4,136,780 | A | | 1/1979 | Hunter et al. | 209/539 |

(Continued)

FOREIGN PATENT DOCUMENTS

DE    195 05 4574 A1    8/1996

(Continued)

OTHER PUBLICATIONS

Greenber, D.S.:"Washington US anthrax scares prompt action on bioterrorism", Lancet, XX, XX, vol. 358, No. 9291, Oct. 27, 2001, p. 1435. ISSN: 0140-6736.

(Continued)

*Primary Examiner*—Hezron Williams  
*Assistant Examiner*—David A. Rogers  
(74) *Attorney, Agent, or Firm*—Lewis, Rice & Fingersh, L.C.

(57) ABSTRACT

Systems and methods for the detection of substances (particularly particulate substances) within mail pieces, specifically letters and other "flats" of mail. In particular, the systems and methods are for the detection of residues of Chemical or Biological Warfare Agents (CBWAs) which may be present within the mail pieces. The system is principally designed to be included as part of Dual Pass Rough Cull System (DPRCS) for the collection and detection of the residue when the contaminated mail piece first enters a mail facility and before it is intermingled with other mail pieces. The system also utilizes aerosol chambers using at least two arrays of pinch rollers to provide for decreased incremental changes on mail pieces and decrease the likelihood of mail piece damage.

28 Claims, 18 Drawing Sheets

U.S. PATENT DOCUMENTS

| | | | | |
|---|---|---|---|---|
| 4,149,622 | A | 4/1979 | Bradshaw et al. | 198/444 |
| 4,275,875 | A * | 6/1981 | Akers | 271/5 |
| 4,718,268 | A | 1/1988 | Reid et al. | 73/19.01 |
| 5,069,440 | A * | 12/1991 | Lazzarotti et al. | 271/202 |
| 5,440,136 | A | 8/1995 | Gomberg | 250/390.04 |
| 5,915,268 | A | 6/1999 | Linker et al. | 73/23.2 |
| 5,992,846 | A * | 11/1999 | Umeda | 271/248 |
| 6,524,846 | B1 | 2/2003 | Robinson | 435/287.4 |
| 6,567,008 | B1 | 5/2003 | Sansone | 340/666 |
| 6,573,836 | B1 | 6/2003 | Gitis et al. | 340/603 |
| 6,613,571 | B1 | 9/2003 | Cordery et al. | 436/48 |
| 6,684,682 | B1 | 2/2004 | Stemmle et al. | 073/23.2 |
| 6,852,539 | B1 | 2/2004 | Cordery et al. | 436/1 |
| 6,729,196 | B1 | 5/2004 | Moler et al. | 073/863.22 |
| 6,742,703 | B1 | 6/2004 | Esakov et al. | 232/45 |
| 6,754,366 | B1 | 6/2004 | Sansone | 382/101 |
| 6,781,078 | B1 | 8/2004 | Das et al. | 209/386 |
| 6,789,727 | B1 * | 9/2004 | Felice et al. | 232/44 |
| 6,792,795 | B1 * | 9/2004 | Jones et al. | 73/37 |
| 6,834,533 | B1 * | 12/2004 | Megerle | 73/45.4 |
| 6,867,044 | B1 | 3/2005 | Cordery et al. | 436/1 |
| 6,888,085 | B1 * | 5/2005 | Spencer et al. | 209/584 |
| 2002/0124664 | A1 | 9/2002 | Call et al. | 73/863.22 |
| 2002/0126008 | A1 | 9/2002 | Lopez et al. | 340/540 |
| 2003/0016362 | A1 | 1/2003 | Megerle et al. | 73/23.2 |
| 2003/0085348 | A1 * | 5/2003 | Megerle | 250/287 |
| 2003/0115998 | A1 | 6/2003 | Belee et al. | 083/343 |
| 2003/0119175 | A1 | 6/2003 | Stradley et al. | 435/287.1 |
| 2003/0136203 | A1 * | 7/2003 | Yoon | 73/864.33 |
| 2003/0144800 | A1 | 7/2003 | Davis et al. | 702/22 |
| 2003/0145664 | A1 | 8/2003 | Schwarz et al. | 073/863.22 |
| 2003/0233891 | A1 | 12/2003 | Cordery et al. | 73/863.21 |
| 2004/0020264 | A1 * | 2/2004 | Megerle | 73/19.01 |
| 2004/0063197 | A1 * | 4/2004 | Tilles et al. | 435/287.2 |
| 2004/0063198 | A1 * | 4/2004 | Tilles et al. | 435/287.2 |
| 2004/0074321 | A1 | 4/2004 | Beck | 073/865.8 |
| 2004/0076544 | A1 | 4/2004 | Dao et al. | 422/62 |

FOREIGN PATENT DOCUMENTS

| | | |
|---|---|---|
| WO | WO 83/00972 A | 3/1983 |
| WO | WO 94/27145 A | 11/1994 |

OTHER PUBLICATIONS

"Biohazard Detection Ssytem" to the United States Postal Service.*
United States Postal Service, Microcadam System Drawing DPRC Converyor System, Aug. 5, 1991, sheets 2, 4 and 5, USA.
Original Filing, U.S. Provisional Patent Application No. 60/334,239, filed on Nov. 29, 2001.
Systems & Electronics, Inc., Dual Pass Rough Cull System, brochure, 2003, USA.
Systems & Electronics, Inc., Automation Systems Group, brochure, 2001, USA.
Original Filing, U.S. Provisional Patent Application No. 60/337,134, filed on Dec. 4, 2001.
Original Filing, U.S. Provisional Patent Application No. 60/330,807 filed on Oct. 31, 2001.

* cited by examiner

US 7,100,422 B2

SYSTEMS AND METHODS FOR RESIDUE COLLECTION WITH IMPROVED LETTER HANDLING CAPABILITY

CROSS REFERENCE TO RELATED APPLICATIONS

This application is a Continuation-in-Part of U.S. patent application Ser. No. 10/449,612 filed May 30, 2003 now U.S. Pat. No. 6,941,794 and currently pending which in turn claims priority to U.S. Provisional Application Ser. No. 60/385,004 filed May 31, 2002. The entire disclosure of both documents is herein incorporated by reference.

BACKGROUND OF THE INVENTION

1. Field of the Invention

This disclosure relates to the field of residue detection. In particular, to the automatic detecting of residues of substances present in letter mail while the mail is in a postal facility.

2. Description of the Related Art

Since the use of Anthrax in the United States Mail in October 2001, government organizations have becoming increasingly interested in detecting dangerous substances such as microorganisms, chemicals, or biological warfare agents which could be distributed through the mail system to promote the agenda of a terrorist organization. As the postal service and mail delivery is a virtually universal service touching the lives of almost all people throughout the United States and many more throughout the world, the postal service presents a potentially limitless distribution network for a terrorist group to utilize. Further, by the time a letter or package has reached the final destination, it has often been handled by many individuals, some of whom may not be known without a lengthy investigation. Any or all of these individuals may have been exposed to the substance and could be affected without rapid medical response. Further, in the case of a contagious substance, trying to quarantine those exposed prior to the contagion becoming epidemic may be virtually impossible.

October 2001 was not the first use of the mail for terrorist acts. Mail bombs and even dangerous pranks, were common long before the mail was used as a method for distributing a biological warfare agent. In addition to purposeful terrorist acts, sometimes dangerous substances are shipped in the mails innocently or for other purposes. Dangerous substances may be shipped by a person who simply does not think of the consequences or the mail may be utilized for other illicit acts such as drug trafficking.

In order to allow the mail to be secure to parties using the mail system for legitimate purposes, mail is sealed and the contents are generally inaccessible to postal workers. This confidentiality is necessary as much of the mail includes confidential information such as financial information and the like and mail which was open could lead to theft of financial information and other important information. At the same time, the sealing of mail can make it difficult for a contaminant to be detected until the mail has reached its prescribed destination and been unleashed.

For the most part, there are no systems designed to screen mail, particularly letters and flats, for contaminants. Existing systems are often limited to large boxes and packages and can only screen for items which can show up on x-ray or similar scanners. These systems, while often effective for detecting bombs, are generally unable to detect powders, liquids, or similar substances which are unlikely to show up on the scans. Oftentimes, the defense to using the mails for terrorist acts is simply to expose the mail to powerful radiation or other decontaminants in the hopes of neutralizing any biologicals present, but this cannot protect against chemical agents and can also damage mail documents. Further, such irradiation is often performed after mail is sorted to protect the recipient, but there may have been many exposed prior to this step.

SUMMARY

For these and other reasons known to those of ordinary skill in the art, described herein are systems and methods for the detection of residues of a substance placed within letters and other "flats" of mail. The system is principally designed to be included as part of Dual Pass Rough Cull System (DPRCS) for the detection of the contaminant when it first enters a mail facility. The system is particularly directed to detecting the residue of a substance or a carrier for a substance but may also detect the substance itself. This system includes letter handling structures comprising two arrays of pinch rollers in the aerosol chamber to decrease the likelihood of damage to mail pieces.

Described herein, in an embodiment, is a residue collection system for collecting residues from the mails, they system comprising: an aerosol chamber including: an internal area; at least two arrays of pinch rollers, each of said arrays comprising two sets of pinch rollers, each array of pinch rollers being capable of compressing a mail piece located within said internal area; and an intake plenum, said intake plenum being capable of collecting air from said internal area and being located between any two of said at least two arrays of pinch rollers; wherein said mail piece passes through a first array of said at least two arrays of pinch rollers, said first array of pinch rollers compressing said mail piece so as to force out some internal air from within said mail piece as said mail piece passes through; wherein said mail piece passes through a second array of said at least two arrays of pinch rollers, said second array of pinch rollers also compressing said mail piece so as to force out additional air from within said mail piece as said mail piece passes through; wherein at least one of said some internal air and said additional air includes a residue of a substance present in said mail piece; wherein said intake plenum can take in at least a portion of said additional air including said residue from said internal area; and wherein said intake plenum can supply said additional air including said residue to a detection system capable of detecting said residue.

In an embodiment, the residue collection system further comprises: a segregation component arranged prior to said aerosol chamber in a mail stream, said segregation component serving to provide said mail piece to said aerosol chamber which may include a cull conveyor or a delayering conveyor. The delayering conveyor may be located after said cull conveyor, may utilize velocity differential separation relative to said cull conveyor or may utilize gravity separation.

In another embodiment of the residue collection system the residue is indicative of a Chemical or Biological Warfare Agent (CBWA) being present in said mail piece or the residue collection system may be part of a Dual Pass Rough Cull System (DPRCS).

In another embodiment of the residue collection system each of said sets of pinch rollers comprises a plurality of disks. One of said sets of pinch rollers in each of said at least two arrays of pinch rollers may be a drive pinch roller and the other is an idler pinch roller at least one which may constructed of a flexible material such as, but not limited to, rubber. At least one of said drive pinch roller and idler pinch roller may have a width between 0.75 and 1.25 inches, more preferably of about 1 inch. In an embodiment, said disks in a first of said arrays are arranged farther apart than said disks in a second of said arrays, which may be touching each other, and the mail piece may pass through said first array before passing through said second array.

In a still further embodiment of the residue collection system the air passes through a cyclonic separator system before reaching said detector. The mail piece may also be a letter or a flat.

DESCRIPTION OF PREFERRED EMBODIMENT(S)

Figure 1:
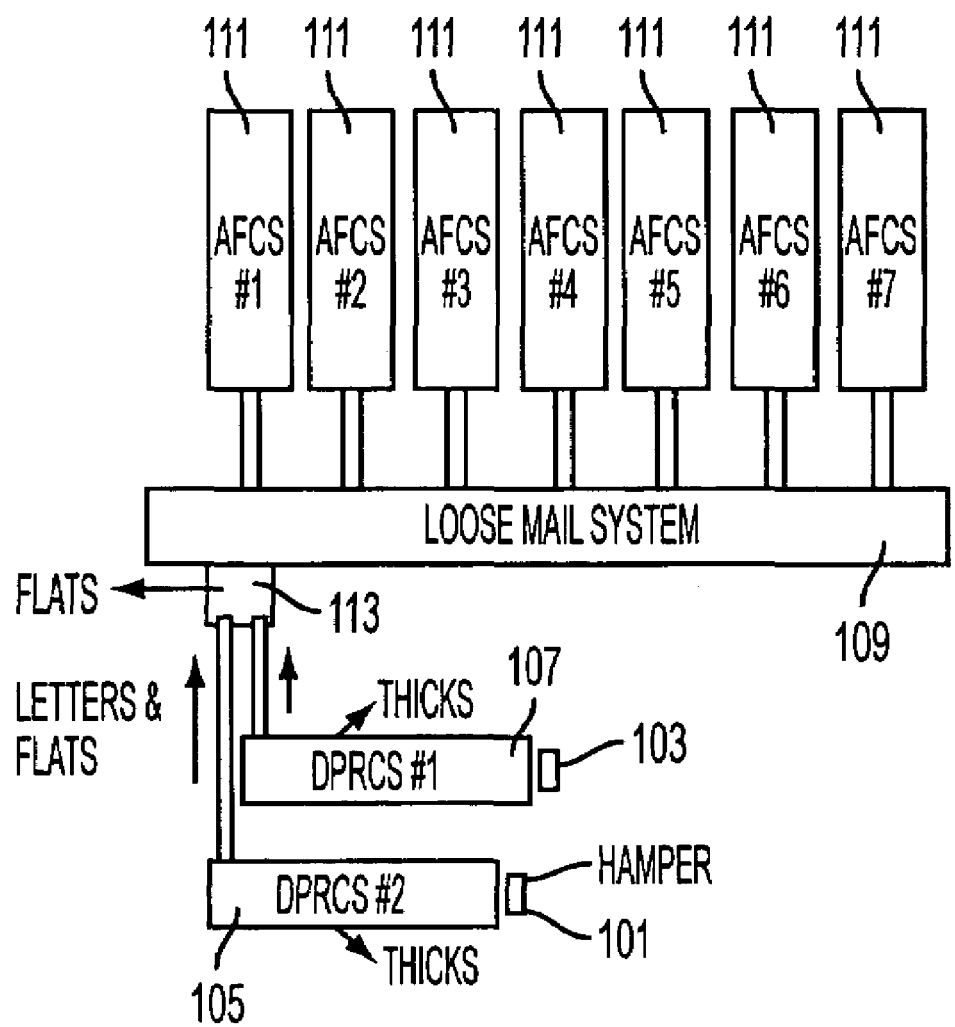
FIG. 1 provides a simplified drawing of an embodiment of a letter collection mail processing facility.
Figure 2:
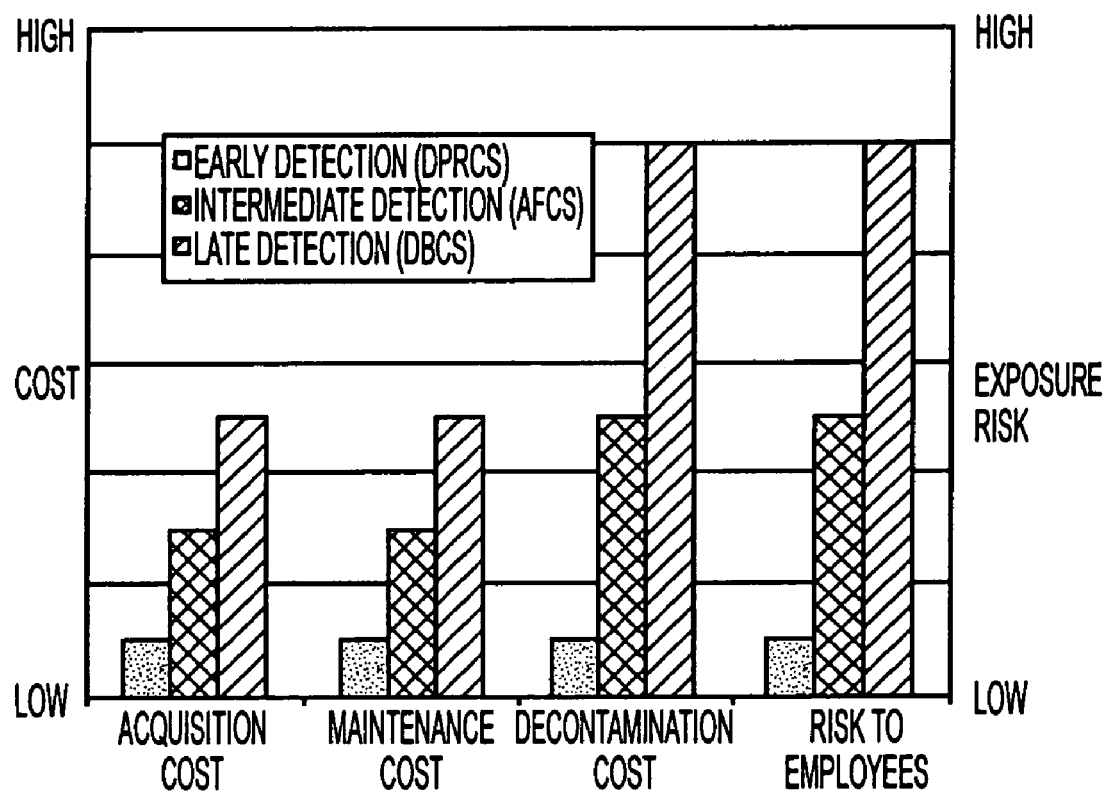
FIG. 2 provides a graph showing an embodiment of how different types of costs are saved by earlier detection of a contaminated mail piece.
Figure 3:
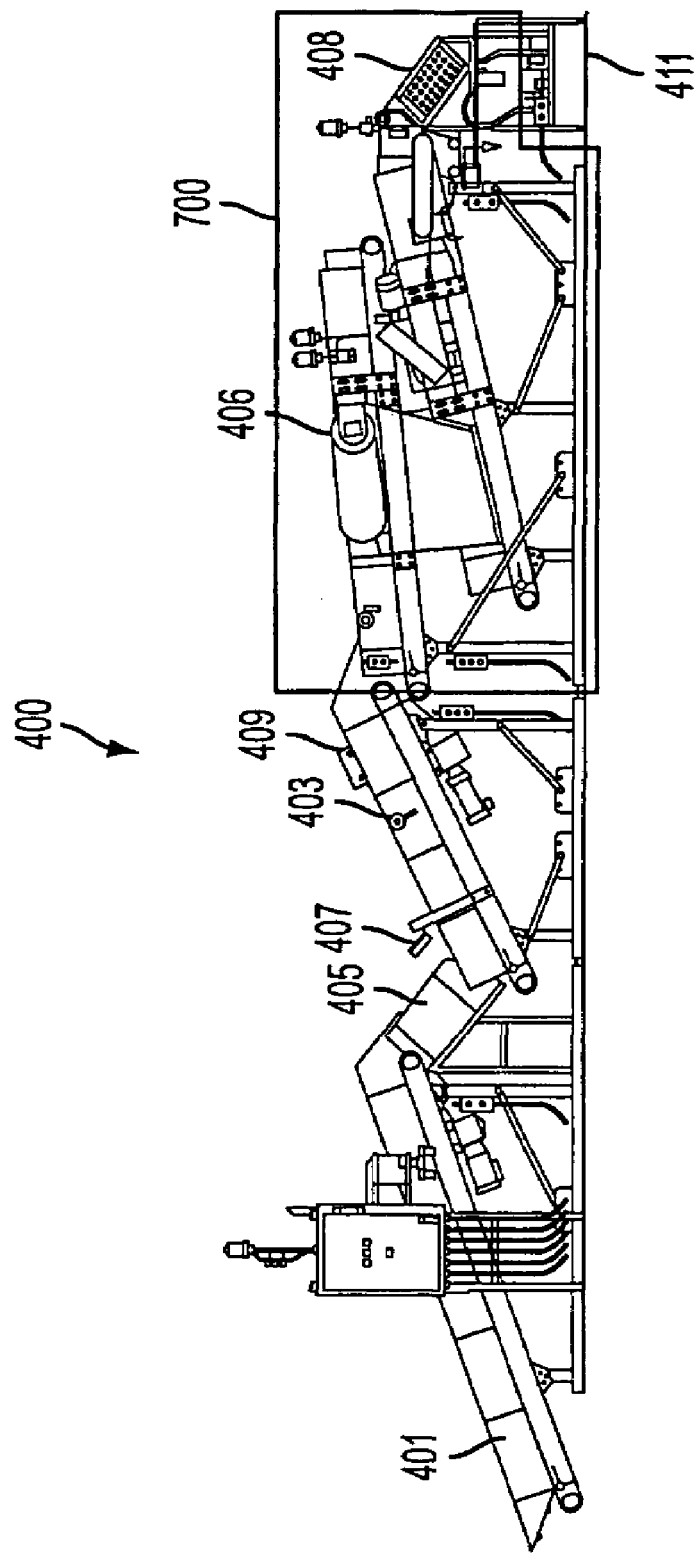
FIG. 3 provides a side view of an embodiment of a Dual Pass Rough Cull System (DPRCS) of the prior art showing the section which is modified by an embodiment of the invention.

While the embodiments described below discuss residue collection modules which are designed to detect Chemical and/or Biological Warfare Agents (CBWAs), one of ordinary skill in the art would understand how the principles, methods and designs disclosed herein can be incorporated to detect other materials in the mail. This can include, but is not limited to, explosive residues, chemicals, drugs, or microorganisms.

The systems and methods discussed will also be primarily discussed as collecting a residue of a substance. For the purposes of this disclosure, a residue is considered to be a small amount of a substance, or a material associated with that substance, generally clinging to the outer surface of the mail from the actions of placing the substance in the envelope. This may exist because the substance has passed over a surface and a small amount of it has been transferred to the surface (via surface tension), has been transferred from fingers or other tools handling the envelope, or may be that a small amount aerosolized in the envelope. A residue can also comprise a small amount of the substance, or material associated with that substance, which can be aerosolized and removed from the envelope by compressing the envelope. A residue may not directly be the substance whose detection is desired, but may be a substance indicative of the presence of the first substance. For instance, the substance or residue may be, but is not limited to, a chemical binder used to particulate a gaseous chemical, or may be a substrate on which a biological is placed.

Further, while the embodiments discussed below are principally for use in conjunction with a Dual Pass Rough Cull System (DPRCS) in the mail service, one of ordinary skill in the art would understand that the system and methods could be used elsewhere in the mail sorting and distribution process. The inclusion in the DPRCS is instead an exemplary embodiment, but one which is generally preferred as it can allow for earlier detection and less exposure than utilizing similar systems and methods elsewhere in the mail distribution process.

With the possibility of over 100 CBWAs that a postal service may wish to screen for, and the myriad of sensor systems presently in development to detect these agents, this disclosure is primarily directed towards devices and methods for collecting a sample of substances in the mail without having to open the mail and without having to expose the mail to potentially dangerous or damaging counter measures which could damage legitimate contents. The number and type of substance detectors used depends upon each detector's capability and the degree of redundancy desired. Extensive research has taken place in the scientific community to develop sensors, which will quickly detect CBWAs or other substances of interest in the air or in water. Sensors are available to identify harmful biological agents as well as chemical ones. Sensors for airborne agents are capable of measuring CBWAs at parts per trillion. Depending upon the sensor technology, analysis can be accomplished anywhere from an hour to near "real time." For the purposes of this disclosure the exact type or number of detectors used to detect the particular substance is not important as the residue collection system of the invention is instead focused to obtaining a sample of a residue (if present) on a mail piece and providing it to the detector so that the detector detects that the substance is present, not with how the detector determines if there is the substance present.

To minimize exposure to employees and reduce cost, a contaminated letter is preferably identified early in the mail processing cycle. The reason for this is that the further the contaminated mail is allowed to travel before it is detected, the more it spreads throughout the facility and the more people who are potentially exposed to it. In the case of a communicable disease or microorganism, for example, as the number of people exposed increases, the likelihood of being able to contain an outbreak can decrease drastically.

FIG. 1 provides a general overview of an embodiment of a mail collection facility. Mail enters the facility in hampers (101) or (103) which are simply large bags or other containers of mail which have been created at the facility or have been transferred to the facility. The hampers (101) and (103) are then dumped into the corresponding Dull Pass Rough Cull System (DPRCS) (105) or (107). At this time, the mail from the hamper (which is from a determinable location) is still together and has generally not come into contact with any mail not originally in the same hamper (101) or (103). As it passes through the DPRCS (105) and/or (107), thicks (packages or boxes usually) are separated out from the letters and flats (large but thin envelopes usually). After the DPRCS (105) and (107), the flats and letters are mixed together and consolidated. A flats takeaway sorter (113) then removes the flats from the mail stream leaving the letters. The letters are spread out among a number of surge and transport conveyors as they enter the Loose Mail Feed System (109). The letters are further spread out as they reach the Advanced Facer Canceller System (AFCS) (111) and ultimately the sorting machines (Not Shown). During this process, the letters, instead of being separated by their pickup points as they are when the process starts, are slowly organized by their destinations and become more and more intermingled.

As the mail spreads out, not only do the number of sensing systems that would be needed to detect a contaminant increase dramatically, but should a contaminated mailpiece be found, the number of mail processing systems that must be decontaminated also rises dramatically as does the number of employees exposed to the potentially lethal agent. Further, it can become harder and harder to localize the source of the contaminant as the source may have contaminated many other mail pieces that it was in contact with. It is therefore desirable to detect the contamination at the earliest possible opportunity. For collection mail, the preferable opportunity for detection is at the DPRCS and therefore in the preferred embodiment the systems and methods discussed herein are designed to be located there.

If the CBWA is detected at the DPRCS (101) or (103), less than 100 feet of conveyor in one system is contaminated. However, if the CBWA is not detected until the AFCS (111) there can be over 1000 feet of conveyor and anywhere from 3 to 10 or more pieces of equipment may be contaminated. The time to decontaminate the facility and the associated cost impact dramatically increases with this later detection.

From an acquisition cost and maintenance, cost perspective, early detection at the DPRCS can result in a 3:1 reduction in the number of detectors. This is a result of the DPRCS being capable of processing 120,000 or more mailpieces per hour while an AFCS can only process 36,000 letters per hour. The initial acquisition cost reduction can be very significant when presently “real-time” CBWA detectors typically cost between $100,000 and $275,000 each just for the basic instrumentation alone.

From a decontamination point of view, the DPRCS is the preferred place to detect any hazardous substance. Isolation and appropriate decontamination procedures can be invoked prior to the mail spreading out and contaminating other pieces of postal equipment. The various increases in costs of detecting as it occurs later in the process is illustrated graphically in FIG. 2.

The following sections describe an embodiment of a Residue Collection Module (RCM) which comprises a device which can be retrofitted into an existing DPRCS, or can be built into a new DPRCS for the purposes of detecting residues associated with various substances of interest (in particular CBWAs) within mail and particularly within flats or letters. One of ordinary skill in the art would understand that the systems, devices, methods and techniques discussed below could be incorporated elsewhere in the postal facility. Such an installation may simply result in increased cost and/or redundancy, and/or may be used for the detection of other substances.

The primary purpose of the RCM is to safely extract and aerosolize a residue associated with a substance or of the substance itself, which may be within, or on the surface of, mail pieces that pass through the DPRCS. The aerosolized mixture is then delivered to a selected detection system for subsequent analysis to detect the substance associated with the residue. The aerosolized mixture which is produced by the RCM is compatible with a wide variety of detection methods as are known to those of ordinary skill in the art, but is preferably suited for those that use an impaction process or other similar method for concentrating an aerosol sample down onto a solid substrate or into a liquid solution.

In the depicted embodiments, the RCM (701) is part of and included as a modification for a DPRCS (400) such as those known to those of ordinary skill in the art. FIG. 3 illustrates the portion (700) of a prior art DPRCS (400), which may be modified during the RCM (701) installation in an embodiment of the invention. The portion that is modified generally contains the cull conveyors (406) and the waterfall assembly (408). FIG. 4 provides an illustration of an embodiment of an RCM (701) which may replace the portion (700) of the DPRCS (400) in FIG. 3. In essence, the modification consists of replacing the indicated portion (700) of FIG. 3 with the RCM (701) shown in FIG. 4. There are some control modifications and an air handling system that are not shown in this FIG. 4, but FIG. 4 shows the principal components of the RCM (701).

The RCM (701) generally maintains the same key functional features of the DPRCS cull conveyors (406) and waterfall assembly (408) while adding the residue collection aspects. Consequently, the RCM (701) need not decrease any of the critical performance metrics of the current DPRCS design. In effect, the RCM (701), when combined with a compatible detection system, can provide the same functions of an existing DPRCS while providing a high level of safety for the loose mail collection operation and the entire facility as well.

The RCM (701) depicted in FIG. 4 includes components which may be eliminated in some embodiments of the invention. In particular, the RCM (701) of FIG. 4 includes two major components. The first of these components is the segregation component (703) which provides for letters to be provided to the second component which is the actual collection system component (800). The Osegregation component (703) may be eliminated or can have numerous other designs in alternative embodiments so long as the letters are provided to the collection system component (800) in a manner that the collection system component (800) can act upon them and collect a sample from them. The segregation component (703) shown in the FIGS (particularly FIGS. 5 and 6) is therefore intended to be exemplary.

Since the RCM (701), in an embodiment, is designed to be an integral part of the DPRCS (400) sorting process, the operation of the RCM is best understood in light of the entire DPRCS operation. The following discussion briefly summarizes the function of the various modules of the DPRCS, how they relate to the overall culling process of mail, and how they relate to the residue extraction and aerosolization process. This discussion is best visualized in conjunction with FIGS. 3–7.

In an embodiment, the DPRCS input is a set of inclined conveyors that are designed to receive mail from standard mail hampers and to deliver this mail in a metered flow to the subsequent culling section. Loose collection mail is dumped from a hopper and enters the DPRCS (400) at the input hopper conveyor (401). Here the mail is moved forward up an inclined conveyor belt where it is temporarily staged until it is called for by the reservoir (405) at the bottom of the next conveyor downstream. The rate of mail being delivered to this reservoir (405) is generally controlled by photocells (407) so that the level of mail within the reservoir (405) remains fairly constant. By doing this, the input hopper conveyor (401) buffers the downstream operation from the rather large fluctuations in mail flow caused by the dumping of mail hampers. This greatly enhances the effectiveness of the next process downstream.

The next conveyor downstream from the input hopper conveyor (401) is the metering conveyor (403). The purpose of the metering conveyor (403) is to provide mail at a steady rate to the next process downstream. As previously described, the input hopper conveyor (401) keeps the reservoir (405) at the bottom of the metering conveyor (403) at a steady level. The metering conveyor (403) pulls mail out from beneath the pile at the bottom of the conveyor. The mail that has been pulled out of the pile forms a layer of mail which slowly advances up the metering conveyor (403).

To adjust for variations in the thickness of the mail layer, feeler gauges (409) near the top of the metering conveyor (403) measure the thickness of the layer and adjust the speed of the metering conveyor (403) accordingly. The metering conveyor (403) will slow down for a thicker layer of mail and will conversely speed up if the layer of mail should thin out. In this manner, the flow of mail at the output end (top) of the metering conveyor (403) remains relatively constant. The flow rate of mail exiting the metering conveyor (403) is operator selectable. The maximum rate for the system is approximately 120,000 mailpieces per hour. The RCM (701) may be designed to handle this maximum mail flow rate.

Figure 4:
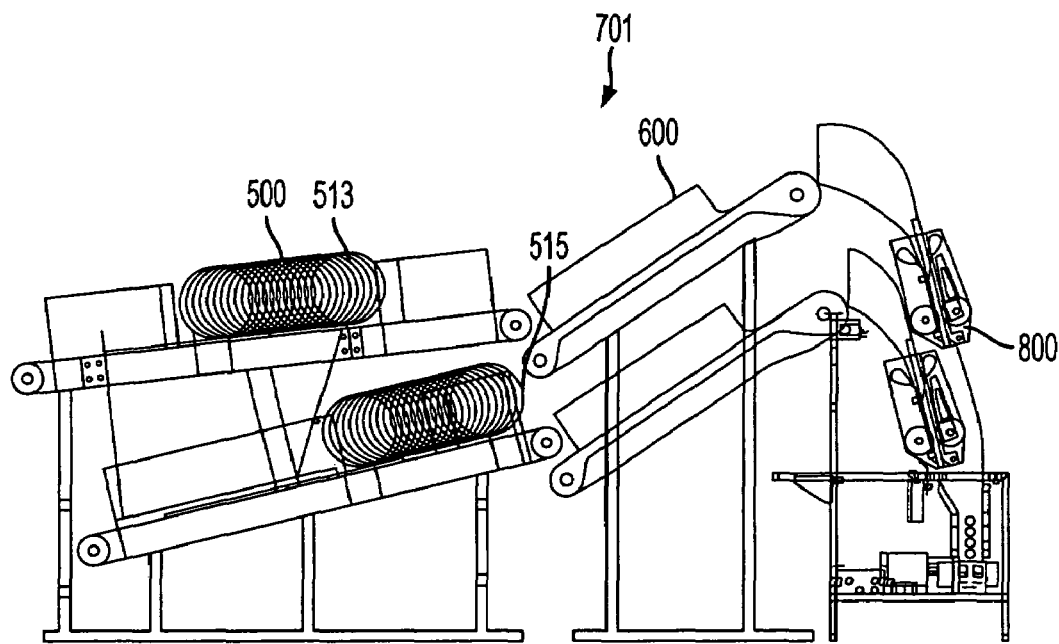
FIG. 4. provides a side view of an embodiment of a modification made to the section indicated in FIG. 3 that provides the principal structure of a Residue Collection Module (RCM).

As the mail drops from the output end of the metering conveyor (403), the mail is considered to enter the portion (700) of the DPRCS (400) which is replaced by the RCM (701). This would traditionally be the culling section. The RCM (701) as shown in FIG. 4 is comprised of three major subsections, their associated controls, and an air handling system. The three major sections are the cull conveyors (500), the delayering conveyors (600), and the collection system component (800). These sections are each described in detail in the subsequent paragraphs as is the air handling system (1100). These sections replace the cull conveyors (406) and waterfall (408) of the prior art DPRCS (400). As the mail exits the DPRCS (400), it is placed on an edge conveyor (411) for transport to the next machine as seen in FIG. 1.

Figure 5:
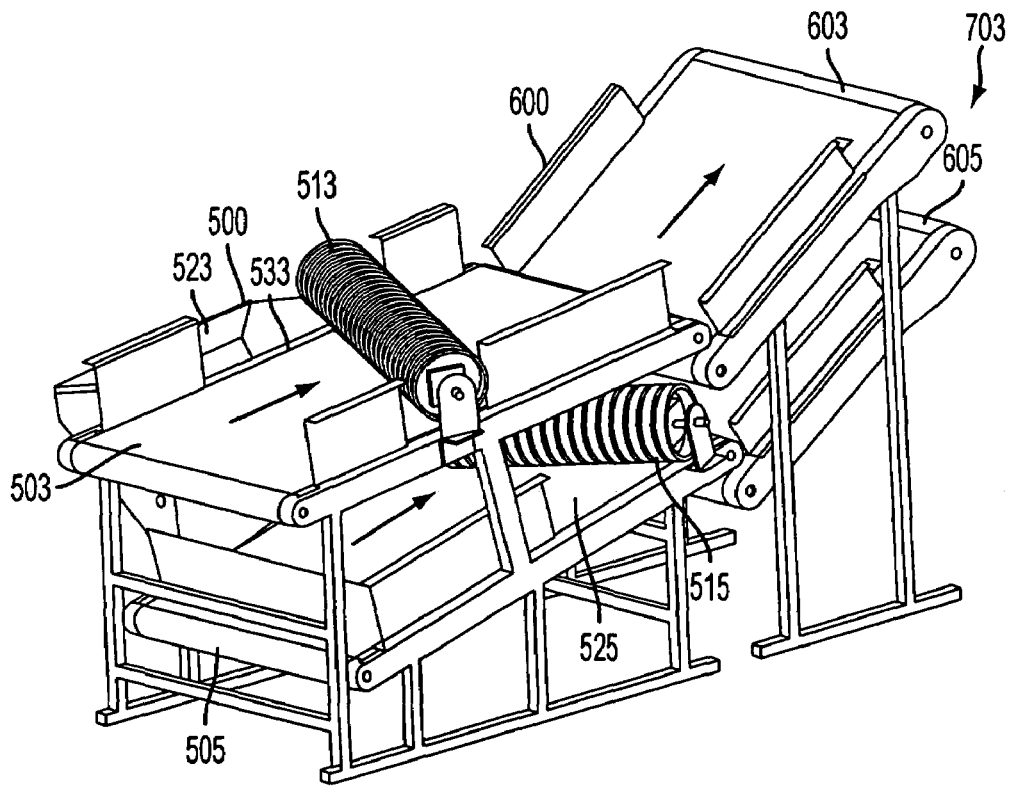
FIG. 5 provides a perspective view of an embodiment of a portion of the RCM of FIG. 4 specifically showing an embodiment of the cull conveyors and delayering conveyors.
Figure 6A:
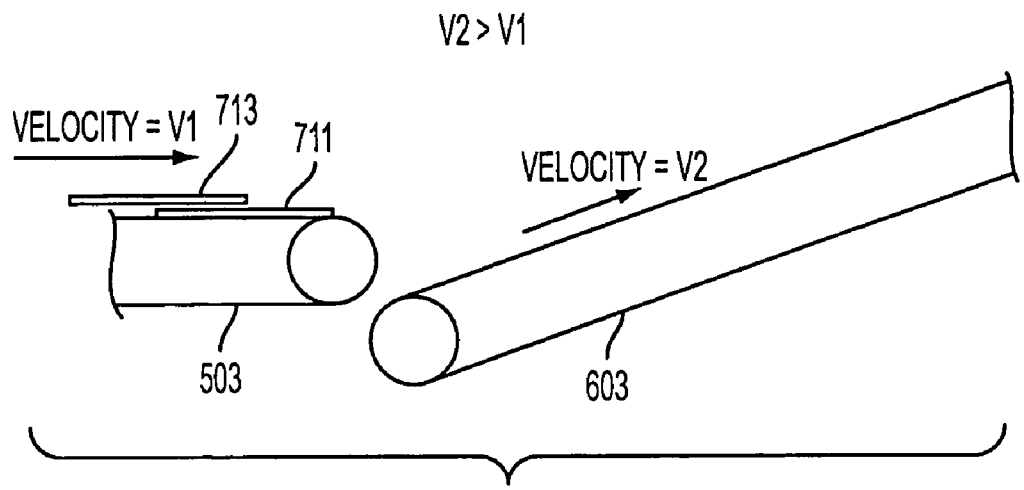
FIG. 6 provides a drawing of how velocity differential separation can work for two layered objects.
Figure 6B:
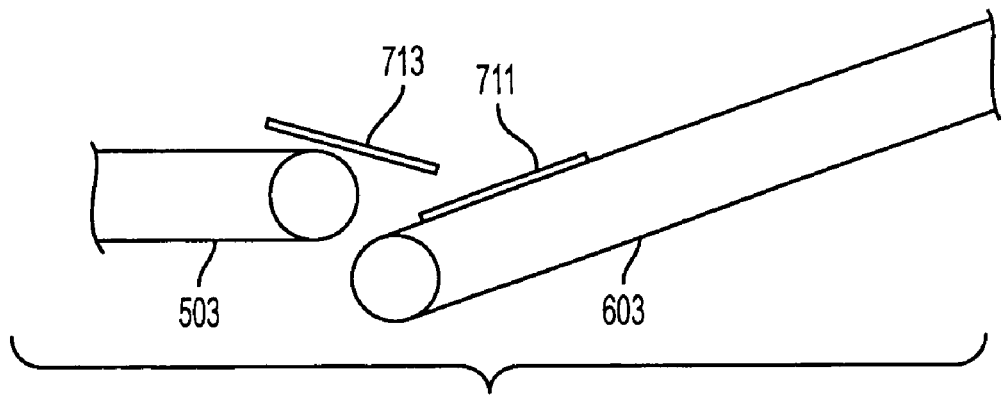
Figure 6C:
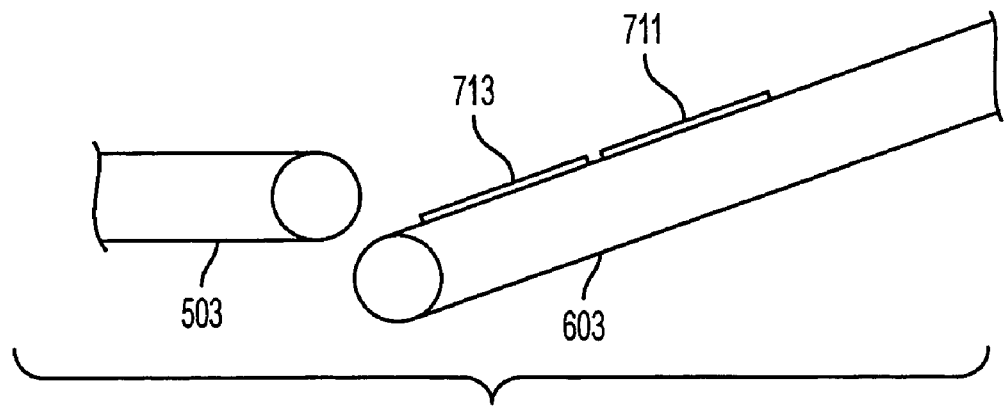
Figure 7:
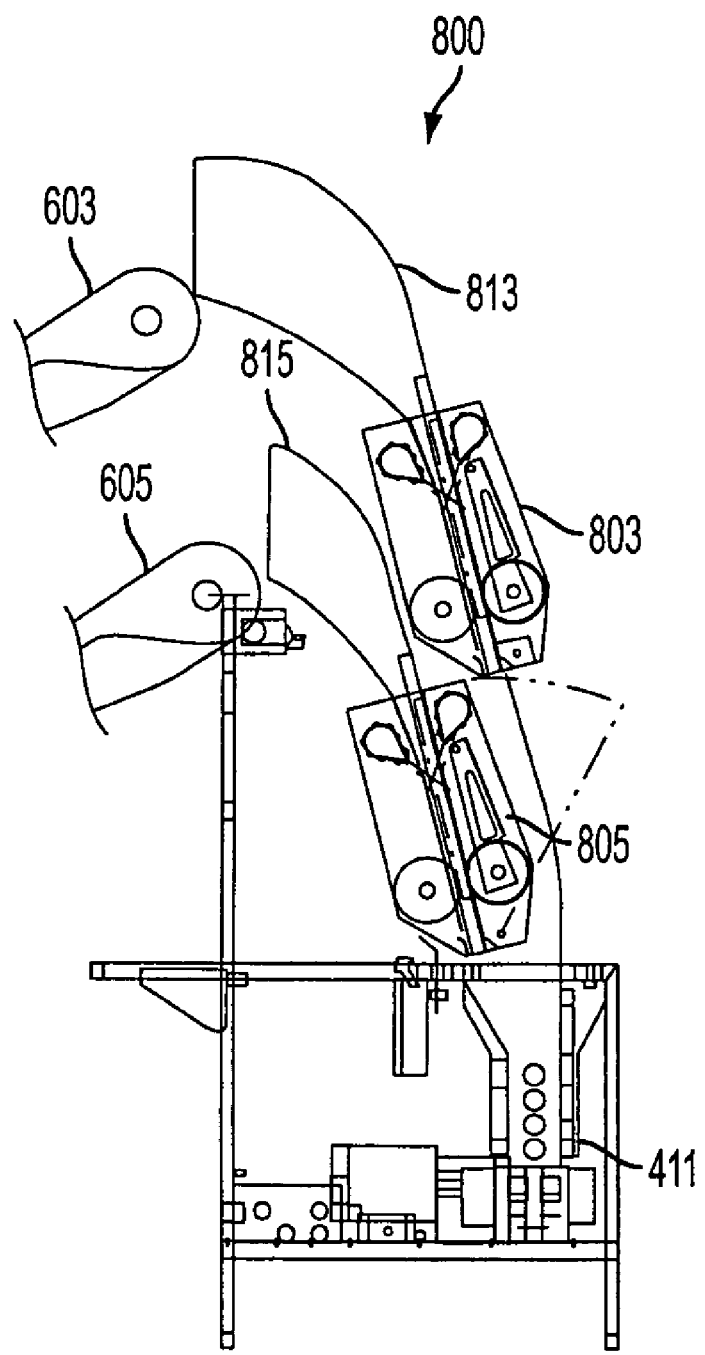
FIG. 7 provides a side cut-away view of an embodiment of a portion of the RCM of FIG. 4 specifically showing an embodiment of the aerosol chambers and waterfall in their closed, operating position.

When the RCM (701) is in place in the DPRCS (400), the mail from the metering conveyor (403) is first provided to the cull conveyors (500). The cull conveyors (500) are similar in design and may be identical in function to the cull conveyors (406) of the present DPRCS (400). The principal purpose of the cull conveyors (500) is to separate out thick mailpieces from the rest of the mail stream and to discharge them onto a separate take-away conveyor which is not shown in the figures. FIG. 5 provides an illustration of the cull conveyors (500) along with the delayering conveyors (600). The cull conveyors (500) are the first set of stacked conveyors. Each of the two cull conveyors (500) in the depicted embodiment comprises a smooth-top cotton belt, or similar conveyor system (503) and (505), with a counter-rotating cull drum (513) and (515) positioned above it. In the illustration, the conveyor motion is from left-to-right and into the figure as illustrated by the arrows.

The metering conveyor (403), described previously, feeds a steady flow of mail onto the top cull conveyor belt (503). The mail is transported forward by the top cull belt (503) until it reaches the top cull drum (513). Mail pieces that are less than a predetermined thickness (generally ⅝ inch) pass beneath the top cull drum (513). Mail pieces that are over the predetermined thickness are deflected by the top cull drum (513) and forced to the side opening (533) of the top cull conveyor belt (503) where they are discharged through a chute (523). During this process, some of the thinner mailpieces which are less than the predetermined maximum are swept off of the top cull belt (503) along with the thicker mail pieces (generally due to the mail pieces being stacked on top of each other as they come off the metering conveyor (403)). The mail discharged through chute (523) is discharged onto the bottom cull belt (505) where the process is repeated with the mail traveling on the bottom cull belt (505) and thicker pieces being deflected by the lower cull drum (515), thus giving thinner mail pieces a second chance to re-enter the major mail stream (the stream of flats and letters). Those pieces which are deflected off both the top and the bottom cull belts (503) and (505) are then discharged onto a "thicks" take-away conveyor (not shown, would be connected to the opening (525)) where they are transported away from the DPRCS (400) to be processed differently. All of the mail, which passes beneath either of the two cull drums (515) or (525) (which comprises the vast majority of the mail collected) is subsequently transported forward to have the residue extraction and aerosolization process performed thereon.

Although the cull conveyors (503) and (505) of the RCM (701) may be functionally identical to those of the standard DPRCS (400), the overall length of the conveyors is preferably shorter. This is done to provide space for the subsequent delayering operation to be described later. The original cull module (406) in the DPRCS is often approximately 151" long. The RCM cull module (500) is preferably only about 86" long. The reduced length may be realized in an embodiment of the invention by reducing some of the conveyor length both before and/or after the actual culling process. All of the critical dimensions in regard to the culling operation, such as cull drum angle and relative position, can be maintained so that the operation of the DPRCS (400) can remain the same.

There is however, one difference between the original cull conveyors (406) and the RCM cull conveyors (500) in the preferred embodiment. On the original cull conveyors (406), the mail on the top conveyor is allowed to fall off the downstream end of the top conveyor (503) and onto the bottom cull conveyor (505). There it recombines with the mail that is already on the bottom conveyor (505) to produce a single mail stream. In the RCM (701), the mail from these two conveyors (503) and (505) is preferably maintained separate, but it is not necessary. As will be described in the next section, this is beneficial for the subsequent mail delayering process.

The output from each of the two cull conveyors (503) and (505) feeds directly onto an associated delayering conveyor (603) and (605). The purpose of the delayering conveyors (603) and (605) is to provide a single layer (or a stream of generally single item thickness) of non-overlapped mail to each aerosol chamber (803) and (805) as discussed later. During normal operation, the mail may arrive at the delayering conveyors (603) and (605) in the form of overlapping "clumps" of mail where one flat of mail is at least partially over another flat of mail, but the thickness is still less than that allowed by the cull drums (513) and (515). In order to maximize the probability that a CBWA will be extracted and aerosolized, these clumps of mail are preferably spread out to form a single layer or close to a single layer of mail by the appropriate delayering conveyor (603) or (605).

The preferred embodiment uses two delayering conveyors (603) and (605) for spreading out the clumps of mail, one associated with each cull conveyor (503) and (505). The reason for this is that the cull conveyors (503) and (505) effectively already perform a preliminary delayering of the mail by spreading the mail out onto each of the two cull belts to a thickness of ⅝" or less. In the prior art DPRCS, the mail on the top belt is then recombined with the mail on the bottom belt, thus defeating the partial delayering achieved by the action of the cull drums (513) and (515). By using two delayering conveyors (603) and (605) and interfacing with the two cull belts (503) and (505) prior to the recombination point, the RCM (701) takes full advantage of the partial delayering effect of the cull drums (513) and (515). In addition, by using two stacked delayering conveyors (603) and (605) instead of just one, the RCM (701) doubles the total amount of available surface area on which to perform the final delayering process, thus greatly enhancing the effectiveness of this operation.

The delayering conveyors (603) and (605) use two principal delayering methods in the depicted embodiment. The first of these methods is velocity differential separation. This is primarily used at both the input and the output of the delayering conveyors (603) and (605). The second method is gravity separation which occurs over the entire length of the delayering conveyors (603) and (605).

The first method, velocity differential separation, is the process of separating the mailpieces by accelerating the lead mailpiece away from the mailpiece that is partially behind it to move them further apart. The speed of the cull conveyors (503) and (505) is preferably a first speed (V1) which in a preferred embodiment is approximately 148 feet per minute (FPM). The speed of the delayering conveyors is preferably set at a faster second speed (V2). The second speed (V2) is preferably approximately 52 FPM faster or around 200 FPM.

FIG. 6 provides an illustration of the velocity differential separation process. In FIG. 6A there is shown two overlapped pieces of mail (711) and (713) approaching the interface of the cull conveyor (503) and the associated delayering conveyor (603). In FIG. 6B there is shown the first mailpiece (711) being fully engaged by the faster delayering conveyor (603) and moving away from the second mail piece (713) that is still under the influence of the slower cull conveyor (503) and gravity. FIG. 6C shows the separation effect on the two mailpieces (711) and (713) caused by the velocity differential at the interface.

While the interface between the cull conveyors (503) and (505) and the delayering conveyors (603) and (605) provides for the primary velocity differential separation, the separation actually takes place at two different locations. The first of these locations, is the input end of the delayering conveyors (603) and (605) at their interface with the cull conveyors (503) and (505) as discussed in FIG. 6. The second location is at the output end of the delayering conveyors (603) and (605) at their interface to the chutes (813) and (815) that feed the aerosol chambers (803) and (805). As the mailpieces fall down the chutes (803) and (805) under the influence of gravity, they are accelerated away from those mailpieces that are still in contact with the delayering conveyor (603) or (605) (which are moving at the speed of the delayering conveyor (603) or (605)). Although the mechanism is somewhat different (powered motion vs. gravity), the principal is still the same.

The second method of delayering is gravity separation. The delayering conveyors (603) and (605) are preferably inclined at a predetermined angle to the surface of the earth. This angle is preferably approximately 30° or greater from the horizontal. The belt material of the delayering conveyors (603) and (605) is further preferably made of diamond wedge belting or of another high-friction belting material. Mail pieces which are in contact with the conveyor belt are pulled forward up the incline because of the friction. Mail pieces which are laying on top of other mail pieces fall backwards under the influence of gravity due to the low coefficient of friction between mail pieces, especially when compared to the interface of the belting to the mail piece. The top mail pieces slide back until they come in contact with enough of the belt surface that they too are pulled forward by the belt surface. The net result is that the mail on the bottom of the layered stream is pulled forward while the mail on the top of the layered stream is retarded due to the force of gravity.

The output of the delayering process therefore is a stream of mail preferably spread across the 4' width of the delayering conveyor so that no two mailpieces are entirely covering one another. This is desired for the aerosolization process, which is to follow, because it is preferable to get access to most of the surface area of each mail piece that passes through the aerosol chambers (803) and (805). The delayering conveyors (603) and (605) generally help to improve the efficiency and detection ability of the detector (1109). However, in an alternative embodiment, the mail may be provided to the collection system component (800) by any method or system known to those of ordinary skill it he art, including, but not limited to, using the prior existing cull conveyors (406) of DPRCS (400).

The primary purpose of the aerosol chambers (803) and (805) and the collection system component (800) of the RCM (701) is to extract a portion of any residue of a substance on the outside of the mail piece as well as a portion of any residue of a substance from inside the mail piece, aerosolize this residue, and deliver this aerosolized mixture to a detection system for analysis. Since the mail upon exiting the delayering conveyors (603) and (605) produces two separate mail paths in the depicted embodiment, two separate aerosol chambers (803) and (805) are also utilized within the collection system component (800) of RCM (701).

FIGS. 7 through 12 and 17 through 22 provide illustrations of different embodiments of the collection system component (800) and the aerosol chambers (803) and (805) included therein. This collection system component (800), effectively comprises the portion of the system which is used to collect the residues. The previously discussed systems are principally designed to organize the mail to be provided to the collection system component (800) in a manner allowing for more efficient operation.

In operation, mail pieces are discharged from each of the two delayering conveyors (603) and (605) and proceed down separate gravity feed chutes (813) and (815) to their respective aerosol chambers (803) and (805). After aerosolization, the two separate mail paths are merged together and the mail generally drops onto the edge conveyor (411) where it is taken to the next sorting machine. After reaching the edge conveyor (411), the residue collection process is generally completed.

Figure 8:
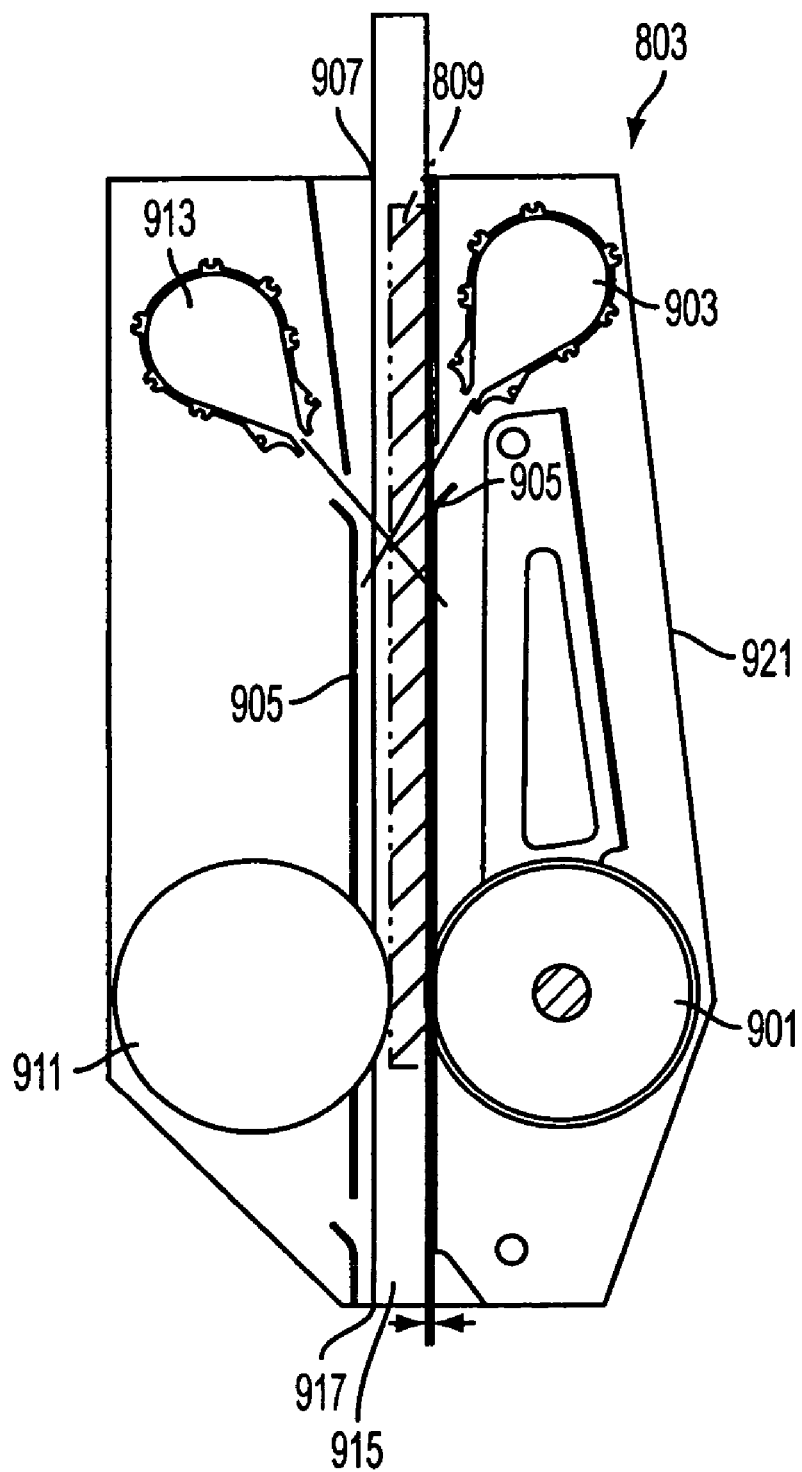
FIG. 8 provides a side, cut-away, view of an embodiment of one of the aerosol chambers of FIG. 7.

A more detailed side view of an embodiment of one of the aerosol chambers (in this case chamber (803) but chamber (805) is identical) is shown in FIG. 8. The aerosol chamber (803) comprises two sets of pinch rollers (901) and (911), a set of air intake plenums (903) and (913), and a set of guides (905) which direct the mail through the chamber (803).

This particular view also shows the chamber (803) with a fairly thick (but flat) mail piece (809) inside of it to illustrate its capacity to handle relatively large flats. The mail piece (809) enters the aerosol chamber (803) from the top (907) after coming down the waterfall chute (813). A set of opposing guides (905) funnel the mail piece (809) past the two opposing intake plenums (903) and (913) which are generally designed so as to draw air from across the entire width of the internal area (915) of the chamber (803). As the air is drawing across the exterior of the mail piece (809) any residue on the exterior of the mail piece (809) is at least partially aerosolized and carried into one of the two air intake plenums (903).

The mail piece (809) then travels between two sets of motorized pinch rollers (901) and (911) which squeeze the mail piece (809) as it passes through. FIG. 8 shows the lead edge of the mail piece (809) just entering the pinch rollers (901) and (911). The squeezing action of the pinch rollers forces out some of the air from within the mail piece (809). A portion of any residue within the mail piece (809) is also generally forced out with the release of this air. Any extracted residue that is released from the inside of the mail piece (809) aerosolizes in the internal area (915) of the chamber (803) and is usually drawn into the intake plenums (903) and/or (913).

The aerosol chamber (803) is preferably held at negative pressure by drawing air into the intake plenums (903) and (913) so that any aerosolized residue from the mail piece (809) is left behind in the internal area (915) of the chamber (803) as the mail piece (809) continues through the pinch rollers (901) and (911) and is ejected out the bottom (917) of the aerosol chamber (803) and into the edge conveyor (411).

Now that the operation of the aerosol chamber (803) has been briefly described, a more complete description of the structure can be made. As mentioned previously, an embodiment of the aerosol chamber (803) is comprised of two sets of pinch rollers (901) and (911) forming a single array of pinch rollers, a set of air intake plenums (903) and (913), and a set of guides (905). These items are preferably enclosed within a housing (921) which may be constructed of sheet metal or another suitable material. The intake plenums (903) and (913) may be commercial off-the-shelf (COTS) items that come in a standard 4' length and are available currently. Each intake plenum (903) or (913) is basically a hollow tube with a slit that runs the entire length of the tube on one side. Air is drawn into the slit and exits out one end of the intake plenum. Air exiting the intake plenum (903) or (913) enters the air handling system (1100) which shall be described later in conjunction with FIG. 13.

Referring again to the embodiment shown in FIG. 8, the sets of pinch rollers (901) and (911) are each slightly different. The left pinch roller or drive pinch roller (911) is preferably a motor driven roller supported by bearings mounted to the air chamber housing (921). It is preferably approximately 5" to 6" in diameter. The tangential velocity of the drive pinch roller (911) is preferably set somewhat greater than the speed of the mail entering the chamber (803) in order to ensure that consecutive mail pieces remain separated during the aerosolization process. Opposite drive roller (911) is an idler pinch roller (901) which may be spring loaded and will generally be free-wheeling as opposed to motorized. This is shown on the right-hand side of FIG. 8 and in FIG. 10. The idler pinch roller (901) not only acts as the opposing pinch roller required to drive the mail piece (809) forward, but it also serves as the mechanism for squeezing the air out of the mail piece (809) to release the residue from within the mail piece (809). Like the drive pinch roller (911), the idler pinch roller (901) is also preferably 5" in diameter. The large diameters on each set of pinch rollers (901) and (911) make it easy for even the thickest mailpieces to pass through unobstructed. In another embodiment, these two rollers (901) and (911) would both be mounted by bearings to the air chamber housing (921) and the pinching action would be supplied by the design of a rubber covering on each roller (901) and (911).

Figure 9:
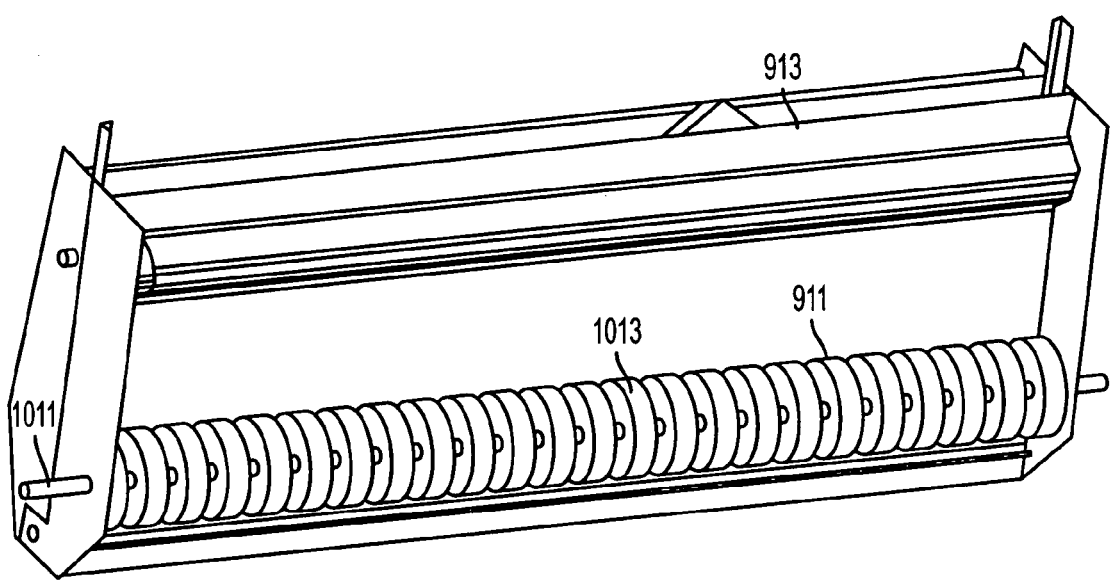
FIG. 9 provides a perspective view of a portion of the aerosol chamber of FIG. 8 particularly showing the arrangement of the drive pinch roller.

A 3D cutaway view of the drive side of the chamber (803) is shown in FIG. 9. Shown in FIG. 9 is intake plenum (913) as well as an embodiment of the drive pinch roller (911). The drive pinch roller (911) comprises of a motor driven shaft (1011), which extends the width of the chamber (803). The shaft (1011) may have a number of disks (1013) mounted on it or may have grooves cut into it. This can allow the mail guides (905) to pass between the disks to provide for the disks (1013) to pass into the internal area (915) of the chamber (803). The grooves between the disks (1013) also provide channels for air to pass through the drive pinch roller (911) as it is drawn toward the intake plenum (913).

Figure 10:
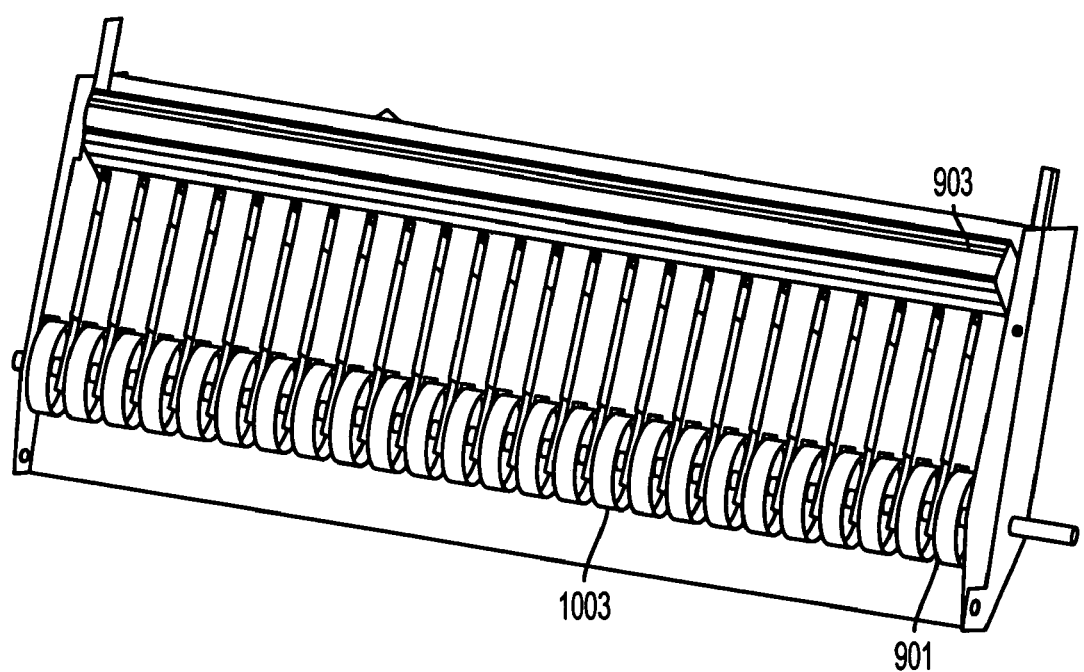
FIG. 10 provides a perspective view of a portion of the aerosol chamber of FIG. 8 particularly showing the arrangement of the idler pinch roller.

A 3D cutaway view of an embodiment of the idler pinch roller (901) of the chamber (803) is shown in FIG. 10. Also, shown in the FIG. 10 is the other intake plenum (903). The idle rollers (1003) match up with the corresponding disks (1013) on the drive roller (911). Each idle roller (1003) may have its own independent suspension to ensure that pieces of varying thickness traveling through the unit side-by-side all get squeezed with the same amount of pressure or they may be mounted on the same suspension system. The idle rollers (1003) are preferably placed on centers no greater than 1.5" apart in order to ensure that even the smallest mailpiece shall have at least one pair of idle rollers (1003) squeezing it.

While this embodiment provides for idle rollers that are spring-loaded so that each mail piece is squeezed even if mail pieces of different thickness pass through side by side, this is not the only way to accomplish effective squeezing. In an alternative embodiment either the drive rollers (911), idle rollers (1003) or both may be manufactured of a resiliently flexible materials such as rubber or flexible plastic. In this case the rollers themselves may compress as the mail piece passes therethrough using their flexibility instead of a specific spring loaded arrangement. This may act in place of, or in addition to, the rollers being spring mounted to provide for effective compression.

Another feature of the aerosol chamber (803) is the guides (905) themselves. These are best illustrated by the side view of the chamber given in FIG. 8. The guides (905) are preferably constructed of sheet metal and form a two-sided funnel to guide the mail piece (809) into the proper orientation and between the pinch rollers (901) and (911). In one embodiment, the guides (905) extend down to a point immediately above the intake plenums (903) and (913). At this point there is an opening (usually about 1" wide) to allow the air in the mail flow to be drawn into the intake plenums (903) and (913). After the opening, a new set of guides (905) continue forward to the pinch rollers (901) and (911). Here the guides (905) may have fingers cut into them so that they can reach through the spaces within the pinch rollers (901) and (911) and pass through to the other side. The guide fingers are generally situated below the level of the pinch rollers (901) and (911) so as not to interfere with the pinching operation. The guide fingers then extend beyond the pinch rollers (901) and (911) a short distance to guide mail pieces through the bottom (917) of the chamber (803).

Figure 11A:
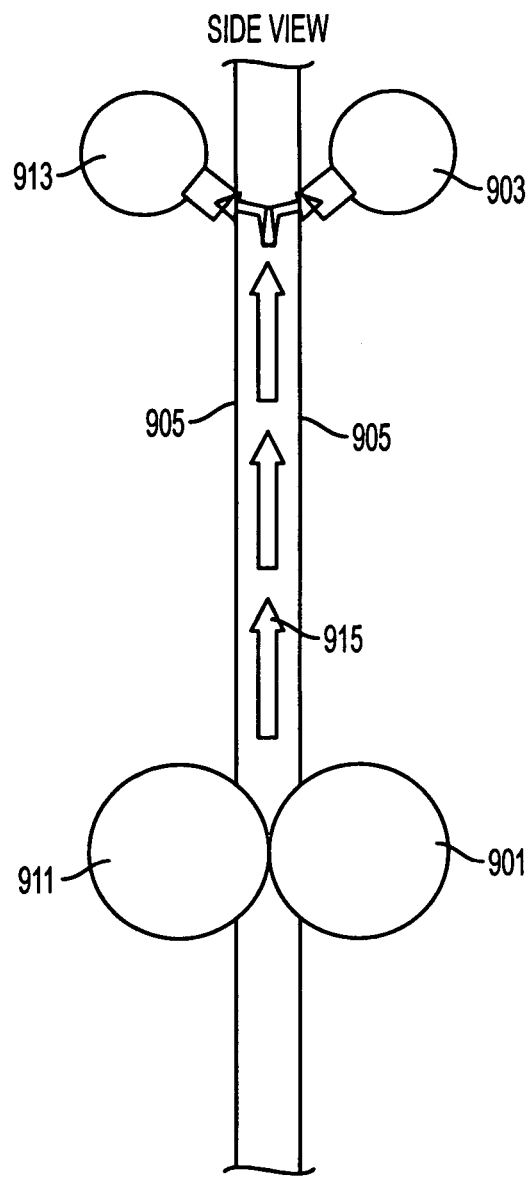
FIG. 11 provides two views (one front and one side) of an embodiment of the air flow through the aerosol chamber of FIG. 8.
Figure 11B:
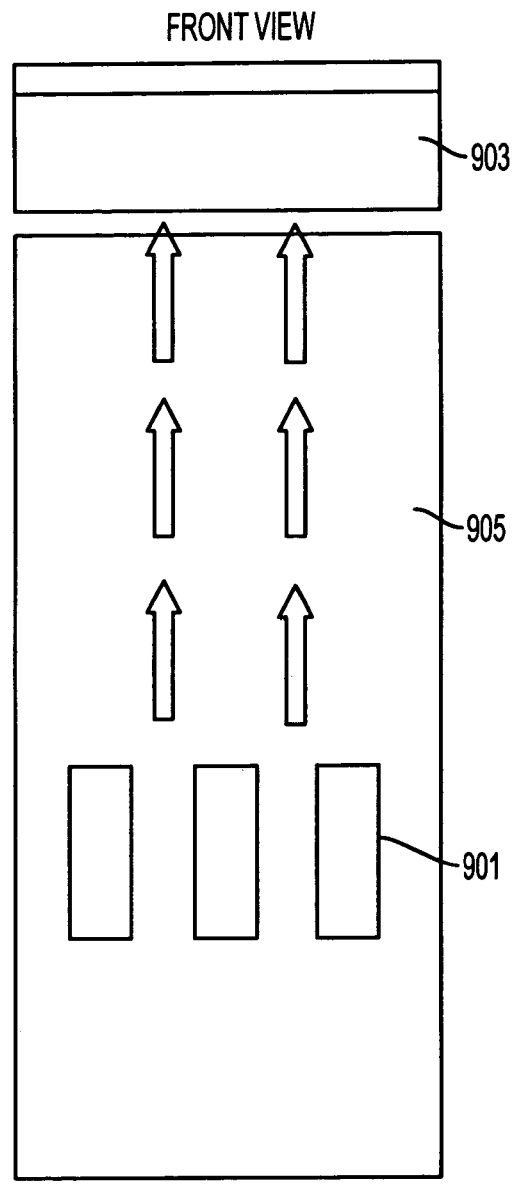
Figure 12:
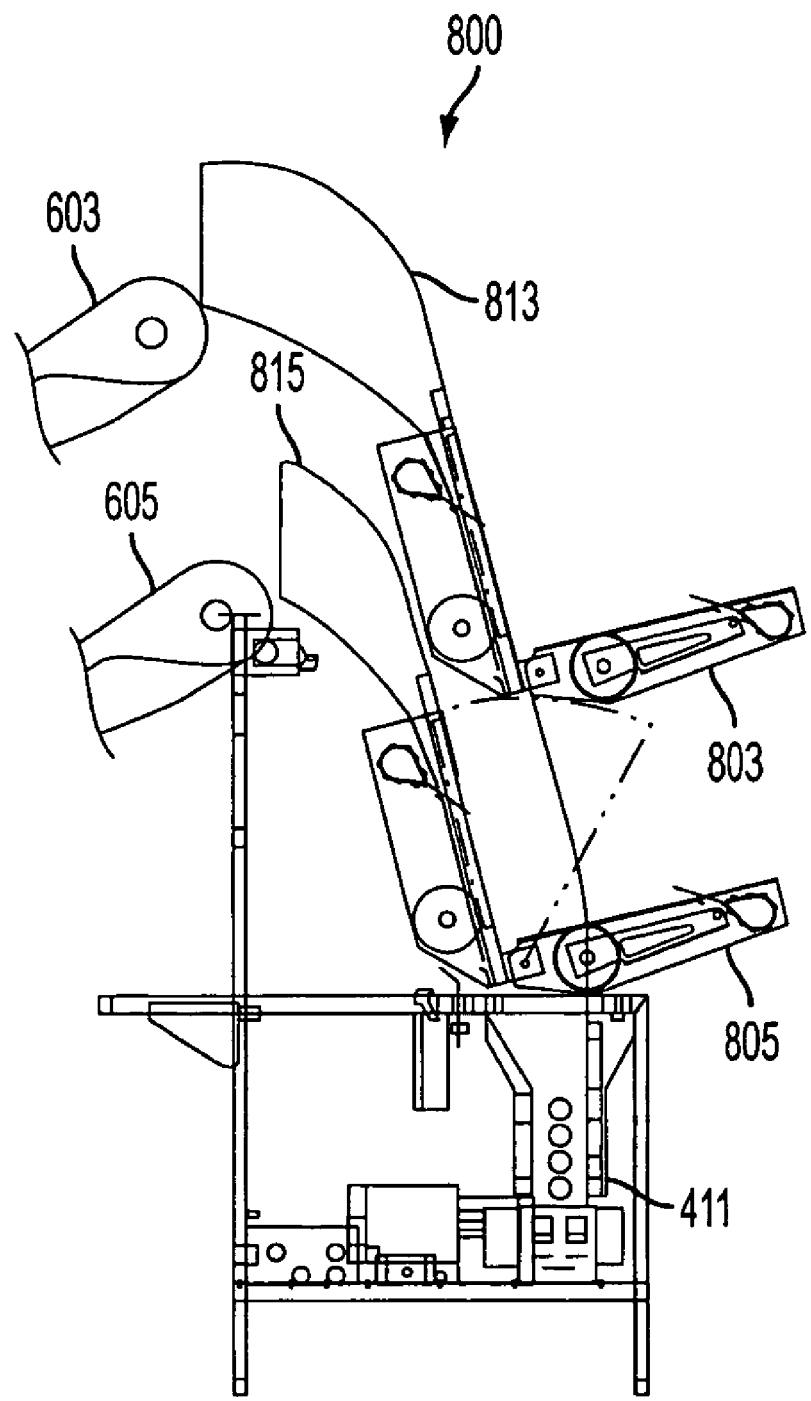
FIG. 12 provides a side cut-away view of an embodiment of a portion of the RCM of FIG. 4 specifically showing an embodiment of the aerosol chambers and waterfall in their open, maintenance position.

A better appreciation of the guides (905) and the effect they can have on guiding the airflow within the chamber (803) is illustrated in FIGS. 11A and 11B. This simplified figure shows, as FIG. 11A, a side view of the chamber (803) including the air flow, and, as FIG. 11B, a front view of the chamber (803) including the air flow. A mail piece (809) passes down the internal area (915) formed by the guides (905), through the pinch rollers (901) and (911), and out the bottom end (917) of the chamber (803). The air travels up the internal area (915) between the pinch rollers (901) and (911) until it reaches the intake plenums (903) and (913). This is shown by the arrows in FIGS. 11A and 11B. The air will often move in a generally laminar flow so that air flows over both the major exterior surfaces of the envelope and generally fills the internal area (915). Further, the flow will be generally from the pinch rollers (901) and (911) to the intake plenums (903) and (913) to prevent residue released from escaping out the bottom (917) of the chamber (803).

Figure 20:
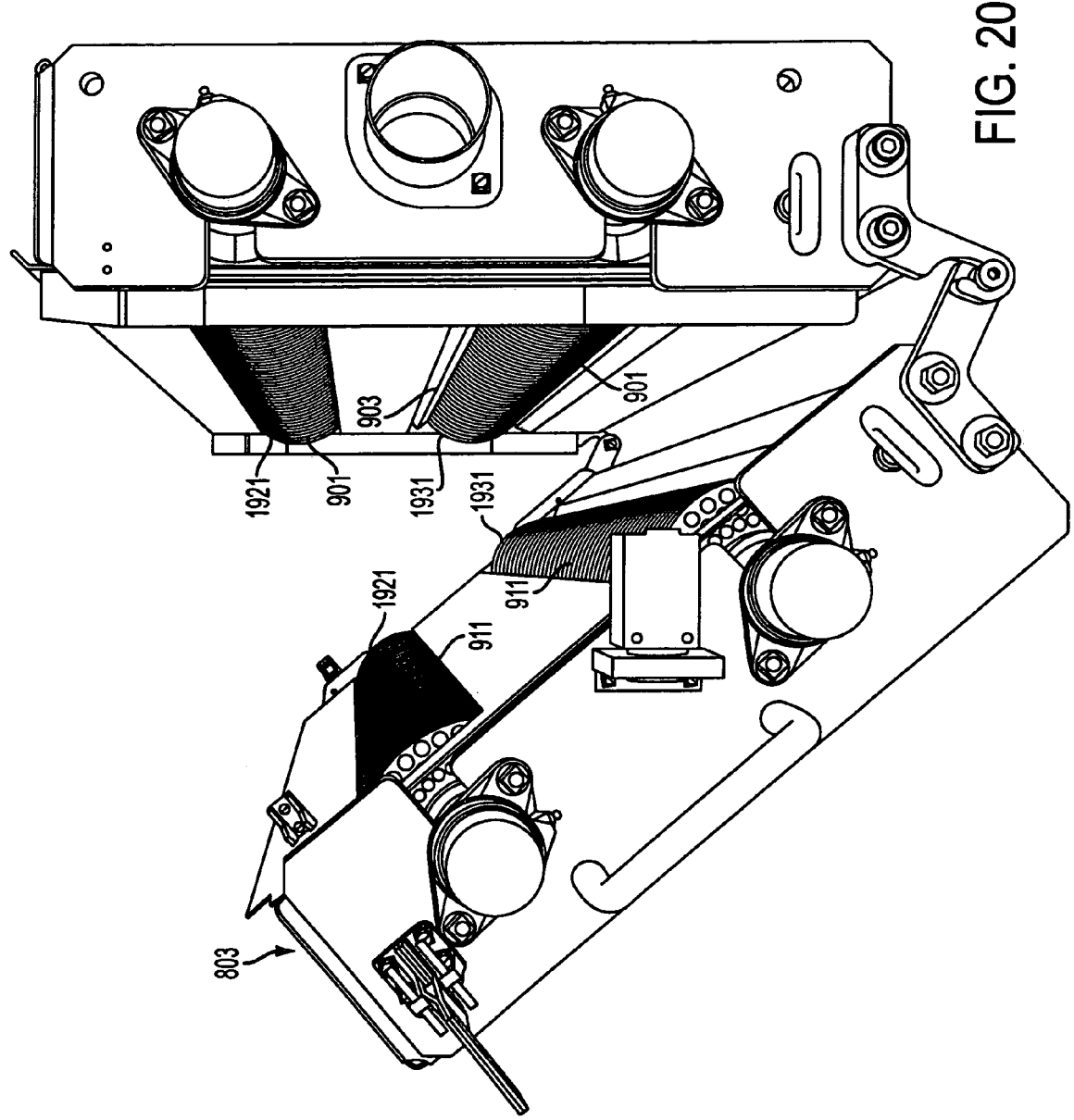
FIGS. 20–22 provide various views of another embodiment of an aerosol chamber as shown in FIG. 7. This embodiment has two arrays of pinch rollers.
Figure 21:
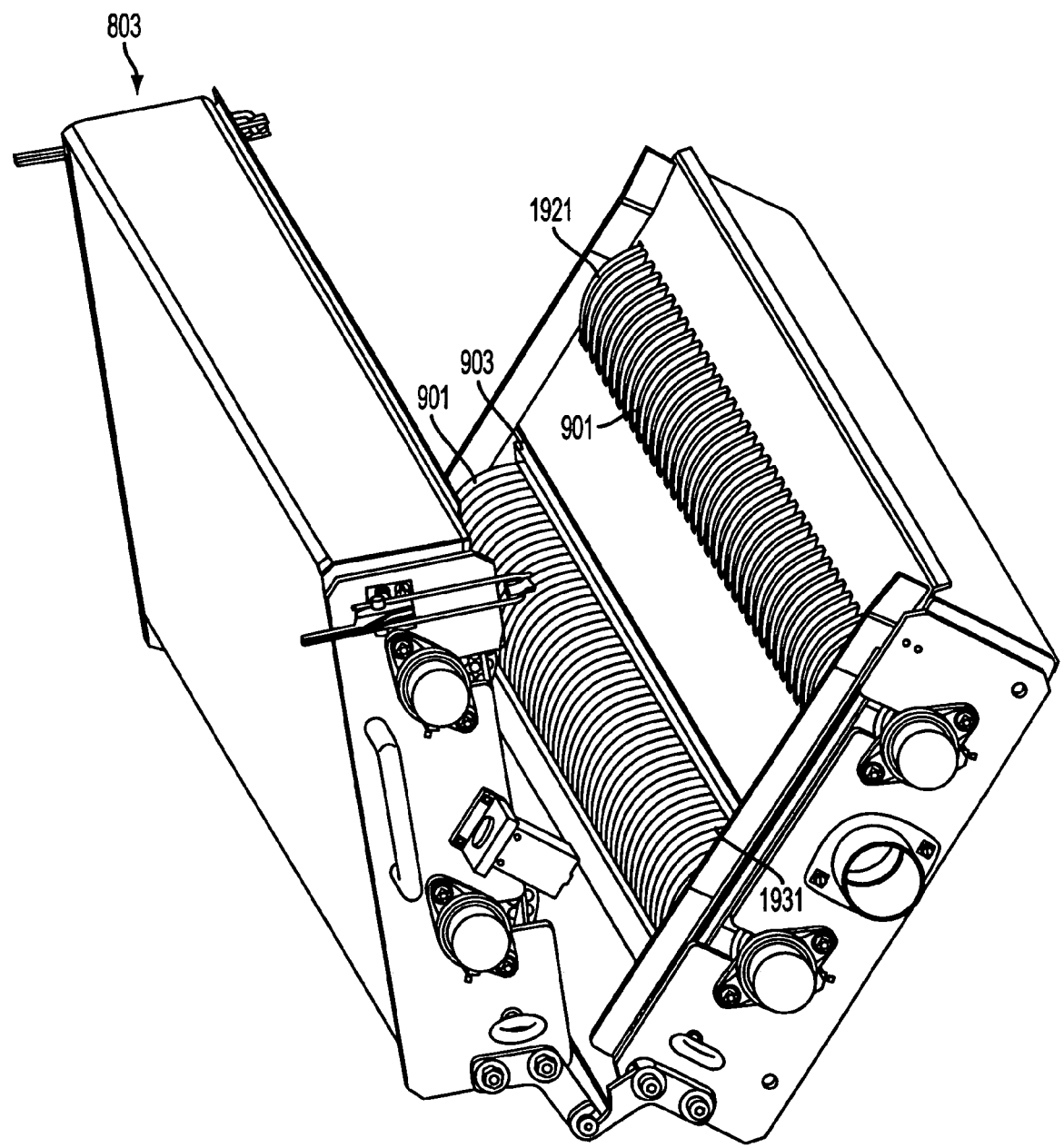
Figure 22:
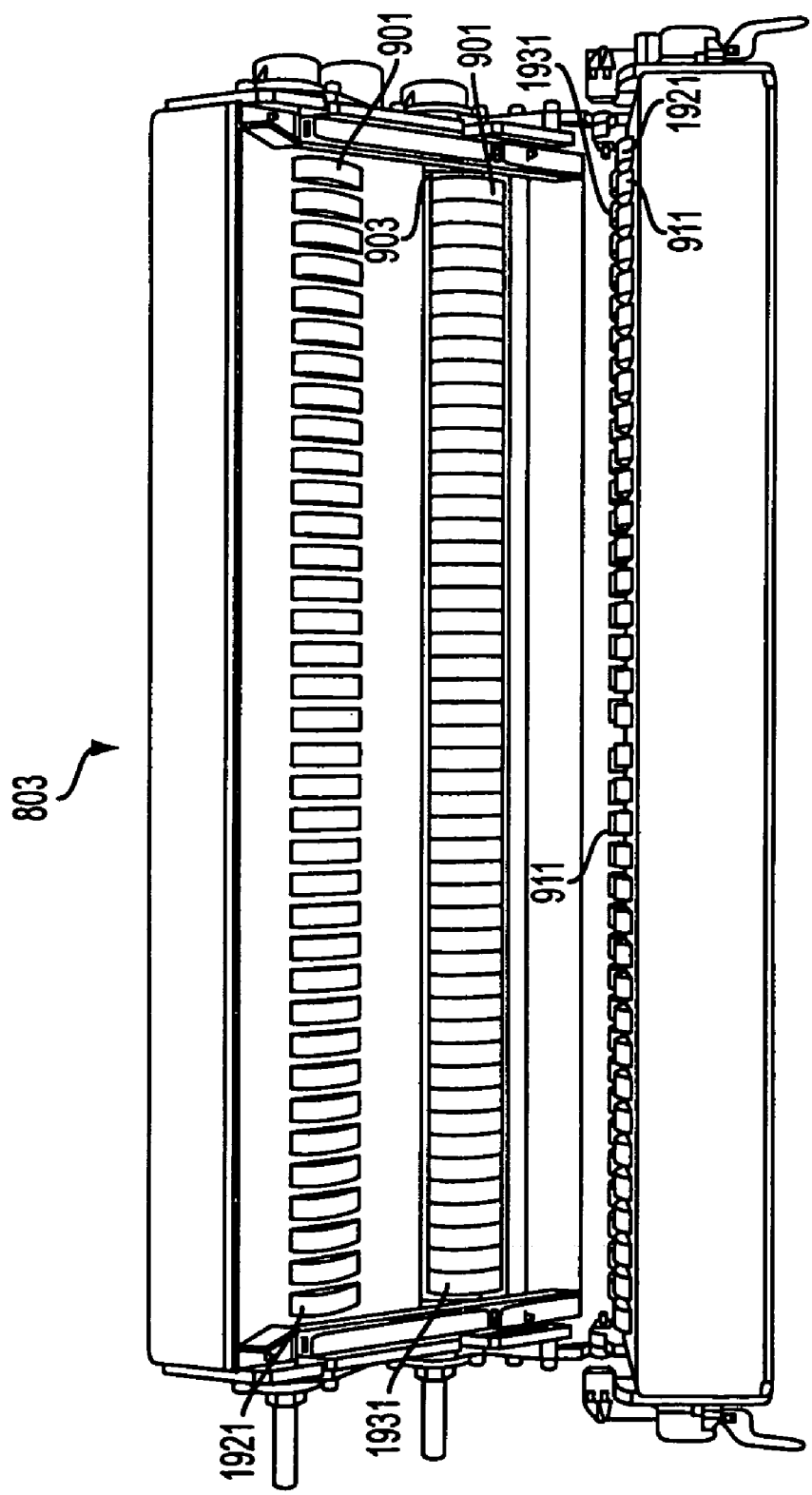

FIGS. 20–22 provide for another embodiment of aerosol chambers (803) and (805). This embodiment provides for two arrays (1921) and (1931) each of two sets of pinch rollers instead of the single array used in the embodiment of FIGS. 8–11. Each array (1921) and (1931) comprises two sets (1901) and (1911) of pinch rollers corresponding to the two sets (901) and (911). Further the intake plenum (903) has been moved so as to be below array (1921) and above array (1931). The two array(s) of pinch rollers (1921) and (1931) are particularly useful because of their ability to compress the mail pieces at a slower pace than when there is a single array of pinch rollers. Further, the second set of pinch rollers (1931) may be arranged so that the disks are closer together to provide for more pinching action in this embodiment. Guides (905) and other structures discussed in conjunction with the embodiment of FIGS. 8–11 may be included in a similar fashion in this embodiment, or may be eliminated.

The first array of pinch rollers (1921) provides for some squeezing of the mail piece which can result in residues being ejected. In an embodiment, the first array of pinch rollers may be of similar design to the single array discussed in conjunction with FIG. 8. Once through this first array of pinch rollers (1921). The mail piece, in the depicted embodiment of FIGS. 20–22 then passes the intake plenum and reaches the second array of pinch rollers (1931), which again squeeze the mail piece to attempt to release any residue which may be present. This second array of pinch rollers (1931) will generally be arranged to squeeze additional air from the mail piece. The mail piece then passes through the bottom of the aerosol chamber (803) or (805) to the edge conveyor as discussed above.

The two array (1921) and (1931) arrangement provides for some benefits over the single array shown in FIGS. 8–11. In particular, because the mail piece is squeezed twice, the first squeezing action can be less than the second with the two squeezing actions can combine to safely squeeze out more air than can be accomplished in the single array embodiment.

If the mail piece is squeezed too quickly as can occur when trying to get sufficient air out of the mail piece in a single squeezing operation, the mail piece can burst as the air being pushed out of the mail piece cannot escape fast enough through existing openings and pressure will cause fractures in the paper. To avoid the bursting problem, less air may be squeezed out which could potentially allow a trace residue to be undetected. The double pinch roller array arrangement of FIGS. 20–22 allows for increased total squeezing pressure at the end of the aerosol chamber (803) or (805) to be provided through two separate squeezing steps resulting in smaller incremental pressures being applied to the mail piece, which, in turn, helps to avoid bursting. In this way, the incremental change on each piece of mail through the aerosol chamber (803) or (805) is less than with a single roller design for the same total pressure. The differential incurred by the mail piece is between the split to two different arrays (1921) and (1931) making each differential less. In particular, if only a single array of rollers is used, all the air is squeezed out at once. If two arrays are used, a lesser percentage of air may be squeezed out by the first array, with the remainder squeezed out in the second array.

A single array of pinch rollers can also present an undesirable jam situation. When the individual rollers are constructed of flexible material, as discussed previously, smaller mail pieces compressed into the rollers can adhere to the rollers' external surfaces. As the mail piece is ejected from the array of rollers, the mail piece may not discharge from the rollers, but may continue to rotate about the roller it is adhered to. This can drive the mail piece into mechanisms or supports for the array damaging mail and possibly jamming the machine. The rate of adherence will generally increase as the pressure applied by the array increases.

The embodiment of FIGS. 20–22 also provides for a different location of the intake plenum (903). In this embodiment, the intake plenum (903) is located between the two arrays of pinch rollers (1921) and (1931), particularly being placed immediately above the second array (1931) in the depicted embodiment. The placement of the plenum (903) between the two arrays of pinch rollers (1921) and (1931) serves multiple purposes. In the first instance, the plenum (903) generally maintains a negative pressure in the aerosol chamber (803) or (805) between the two arrays of pinch rollers (1921) and (1931). Therefore, particulates released by both arrays of pinch rollers (1921) and (1931) will be pulled toward the plenum (903) (generally between the rollers of the first array (1921) if released by the first array (1921)). This arrangement is useful as the second array of pinch rollers (1931) is preferably arranged so as to have little to no space between the rollers in the array providing for little chance for air to escape and contaminants to reach the surrounding atmosphere.

In particular, as a mail piece passes through the first array of rollers (1921), the compression of the mail piece will generally release only easier to release particles from the mail piece and will not eject all the air from the mail piece. This air will be ejected above the upper array of pinch rollers (1921) and will be sucked downward into the plenum (903)

by the negative pressure created by the plenum (903). The particulates and air released will generally flow between the rollers on the array (1921), as discussed in conjunction with FIG. 11, and toward the plenum (903).

Further, the initial pinching action of the first array (1921) (or the re-expansion after pinching) may serve to disturb particulates in the mail piece stirring them into the air in the mail piece even if they are not ejected. The mail piece is then further exposed to the generally negative pressure of the center section. The negative pressure will generally cause particles on the mail piece, or those in the mail piece which were stirred, to be pulled from the mail piece.

As the mail piece goes through the transition space between the two arrays of pinch rollers (1921) and (1931), it has already been partially flattened by its passage through the first array of pinch rollers (1921). However, as it has not been completely compressed against the first array of pinch rollers (1921) it is unlikely that the mail piece will adhere to the surface of the rollers as can be the case during strong fast compression. Because the compression pressure can be less than in the single array, the mail piece will instead generally continue on a linear track between the two arrays of pinch rollers (1921) and (1931) as the pressure is not sufficient to cause adherence.

The second array of pinch rollers (1931) will impart additional squeezing on the mail piece forcing more internal air out of the mail piece and toward the intake plenum (903). This additional squeezing will generally apply more pressure to the mail piece than what was applied by the first array, although, in an alternative embodiment, similar pressure (or less pressure) may be used as any of these still results in additional compression. The use of the phrase "additional squeezing" is to refer to the fact that the letter is squeezed a second time, not necessarily that more pressure is used. This additional squeezing can eject more smaller particles (which will often be of more interest) to the intake plenum (903) from the inside of the mail piece or eject particles aerosolized in the first squeezing but not ejected. This is particularly valuable if the residue of interest is of small size in particulate form in the mail piece.

The second array of pinch rollers (1931) will generally comprise rollers that are significantly closer together that in the first array of pinch rollers (1921). This design is preferred as it allows for additional air to be compressed from the mail piece, hopefully approaching all of the air originally in the mail piece being squeezed out. So as to supply sufficient pressure, the second array of pinch rollers (1931) will generally comprise rollers spaced closer together than in the first array of pinch rollers (1921). In an embodiment, there is no space between the rollers which are arranged directly side by side. The rollers will however, still be spring mounted, or may be of compressible material, to allow for mail pieces of different sizes to pass simultaneously side by side and still be squeezed. While this array may actually squeeze a net of more air from the mail piece than would be squeezed in a single array case, because this array is second, the mail piece has already been partially compressed and is therefore less likely to adhere or suffer from bursting.

The two array pinch roller (1901) and (1903) embodiment of aerosol chambers (803) and (805) therefore will generally provide for an improved sampling of residues, as well as for an improved mail handling ability over that of the single array pinch roller system shown in FIGS. 8–11 by decreasing the number and severity of damaged mail pieces by adherence or bursting and by decreasing the likelihood of a jam from a mail piece adhering to an array of pinch rollers. The decrease in damage is generally attributable to a decrease in incremental pressure without having to decrease total pressure applied. As would be apparent to one of ordinary skill in the art, however, either embodiment of aerosol chamber (803) or (805) may be used in the system depending on the characteristics desired. Still further, in another embodiment, more than two arrays of pinch rollers may be used in each aerosol chamber (803) and (805). Such a larger number of arrays can provide for even smaller incremental changes.

Figure 13:
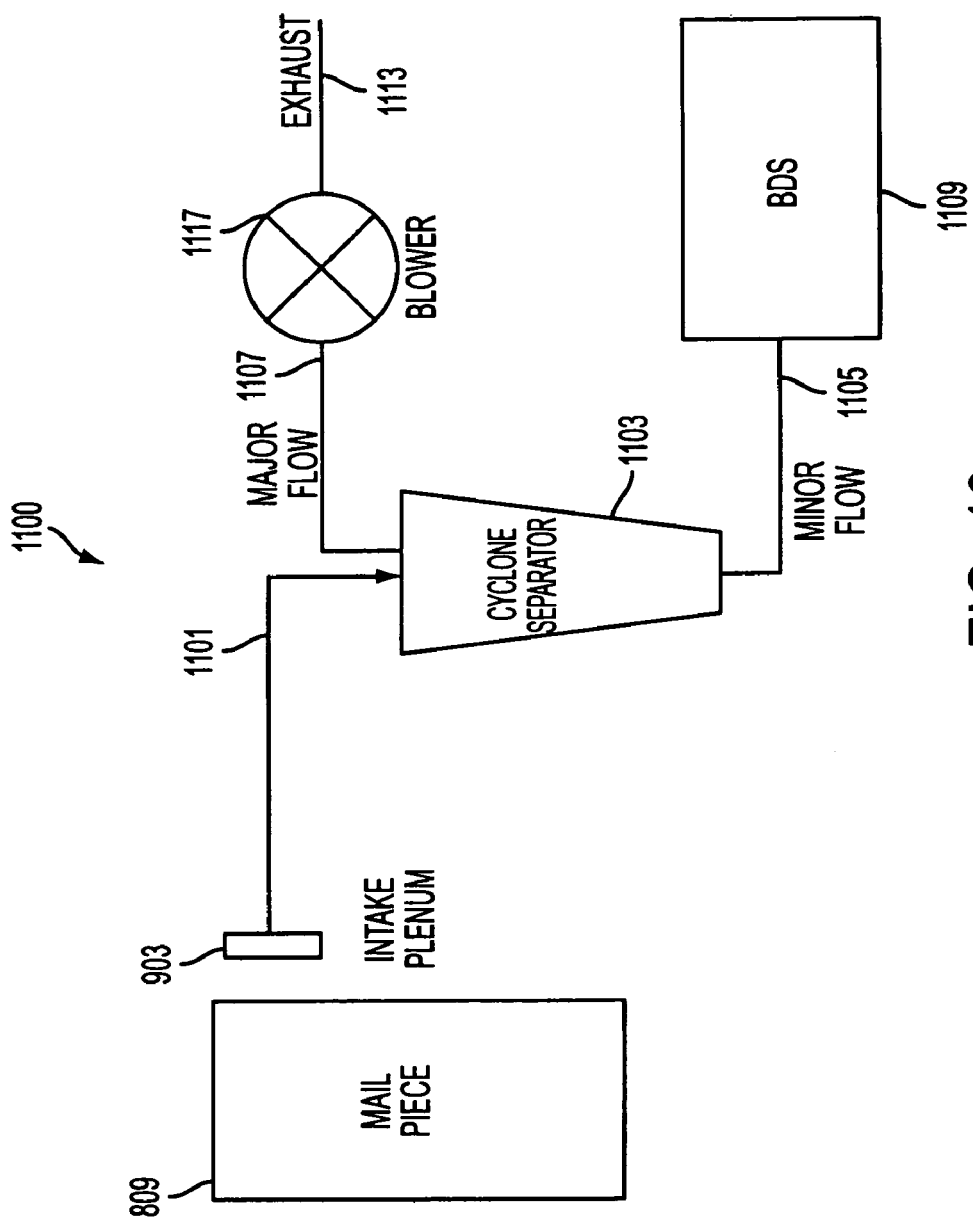
FIG. 13 provides a schematic diagram of an embodiment of an air handling system for use with the aerosol chambers of FIG. 8.
Figure 14:
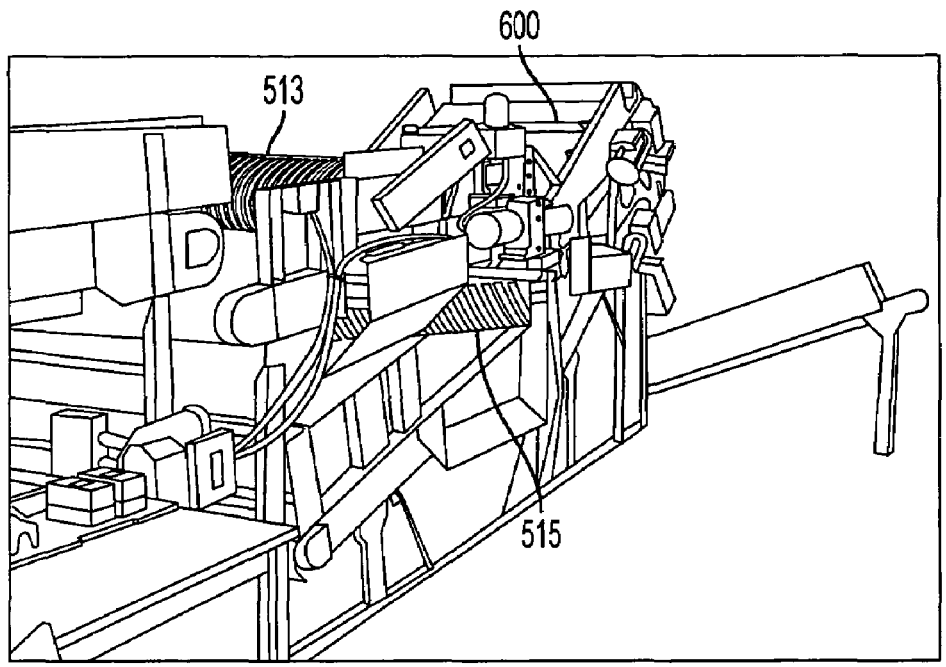
FIGS. 14–19 provides an embodiment of an RCM and air handling system forming a portion of an embodiment of a DPRCS.
Figure 15:
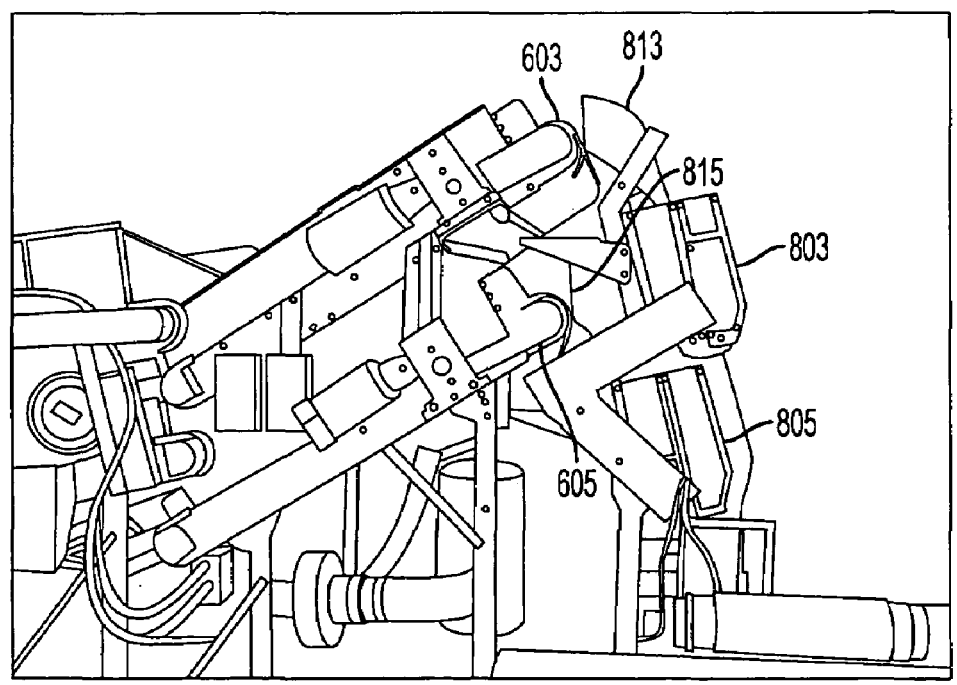
Figure 16:
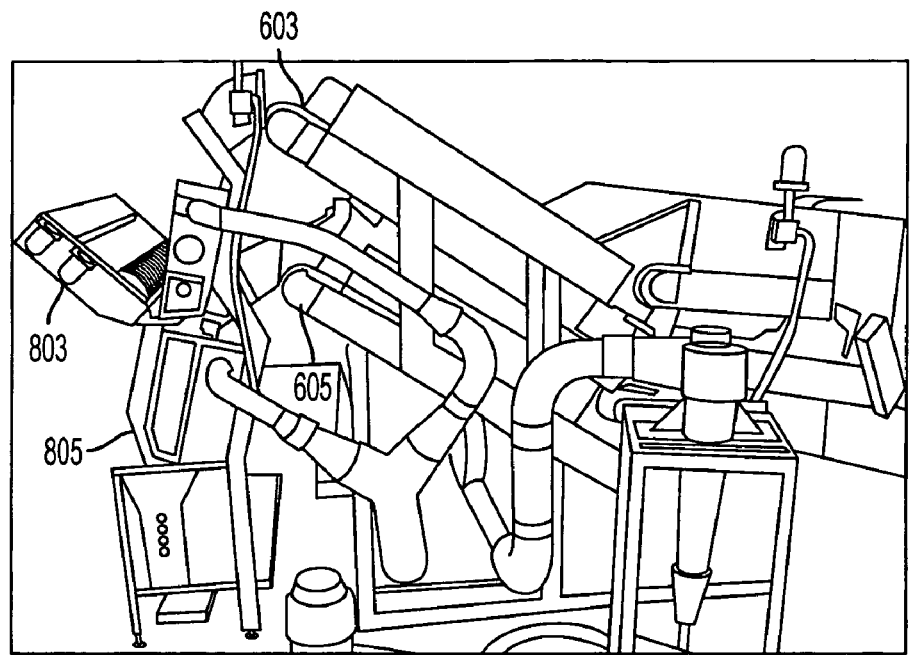
Figure 17:
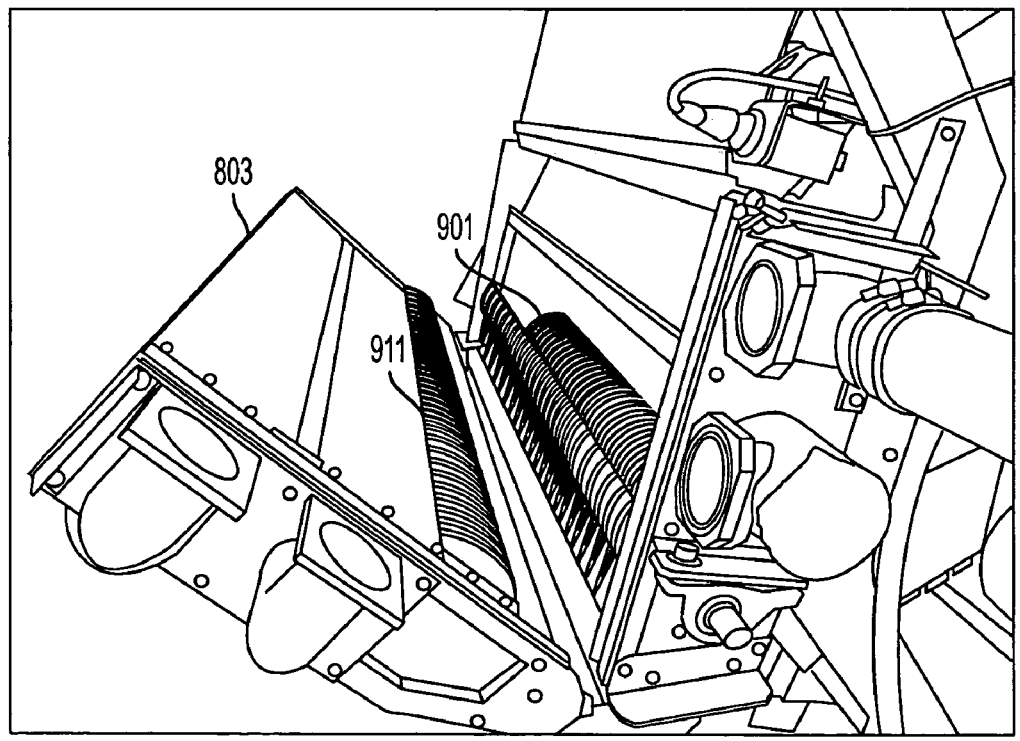
Figure 18:
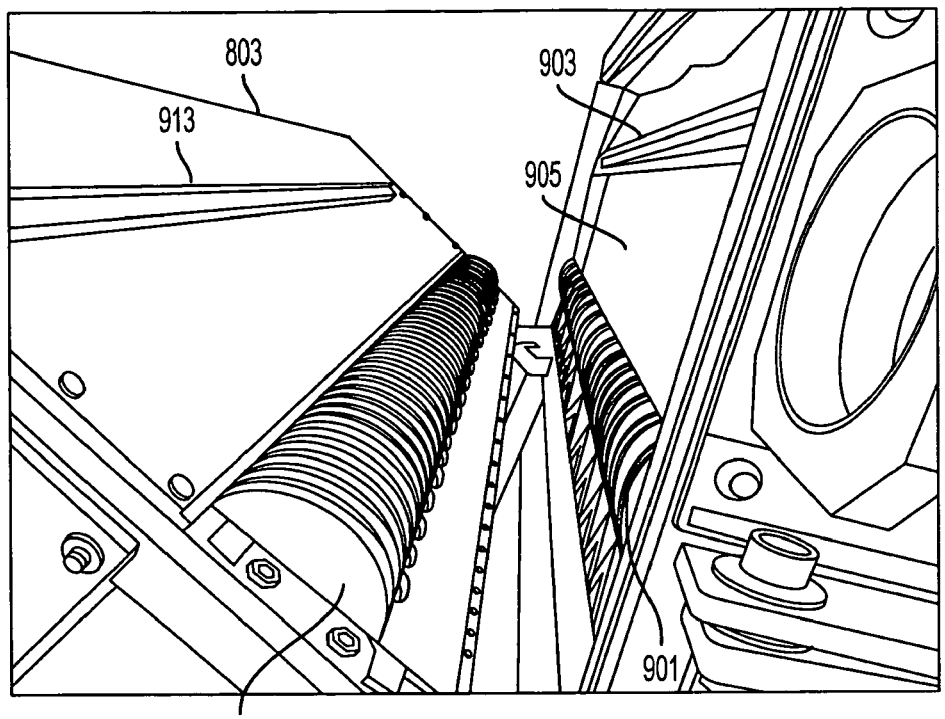
Figure 19:
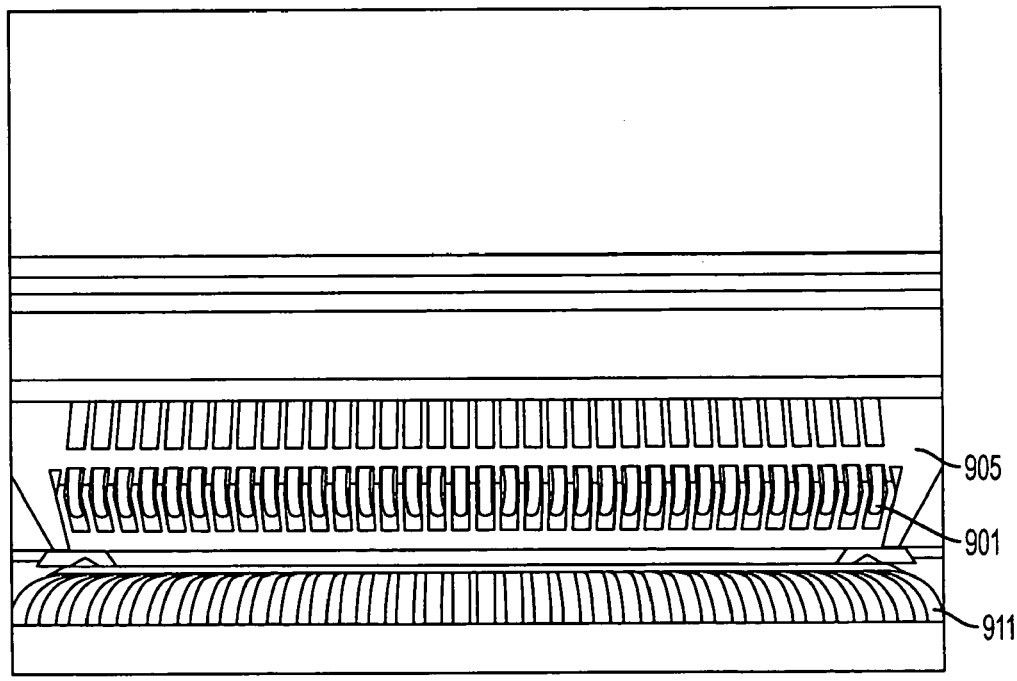

The air collected from the mail piece (809) in the input plenums (903) and (913) (which contains the aerosolized particles of the residue if one is present) is then preferably removed from the input plenums (903) and (913) and the main body of the RCM (701) by an air handling system (1100) which provides the air to the selected detector (1109) for evaluation and detection of the residue. FIG. 13 is a schematic diagram of an embodiment of an air handling system (1100) which may be associated with one or both of the aerosol chambers (803) and (805) and with any embodiment of aerosol chambers. For clarity purposes, the embodiment of FIG. 13 will be discussed as attached to chamber (803) and to only one intake plenum (903). One of ordinary skill in the art would understand how the air flow from related components is generally similar to this case regardless of how the air handling system (1100) is attached.

In the depicted embodiment of the air handling system (1100), air entering the intake plenum (903) is routed through duct work or other air transport devices (1101) and delivered to a flow cyclonic separator system (1103). The design of the cyclonic separator system (1103) preferably operates in accordance with systems and methods described in U.S. Provisional Patent Application Ser. No. 60/560,122 the entire disclosure of which is herein incorporated by reference. However, one of ordinary skill in the art would understand how other cyclonic separator systems could be used. The cyclonic separator system (1103) is designed to concentrate particles of a size of interest corresponding to the desired residues (preferably 0.8 micron and larger particles). Particles of the size of interest are sent down a flow duct (1105) and delivered in an aerosolized form through to a detector system (1109). The detector system (1109) preferably operates at a flow rate of 400 to 450 liters per minute but the air handling system (1100) can accommodate detector systems (1109) utilizing flow rates other than this.

Particulates not of the specified interest area, are cycled through a flow duct (1107) and exhausted (1113). The blower (1111) helps to pull the air from the chamber (803) into the air handling system (1100). The exhausted air may be returned to the surrounding air, or may be filtered and/or neutralized and reused in the system, or disposed of.

In another embodiment, the air-handling system (1100) would not use the cyclonic separator system (1103) but instead would duct the air from the intake plenum (903) directly to the detector system (1109). This air-handling system (1100) may be employed if the air flow rate and sensitivity of the detector system (903) allowed the use of such a system.

The output of the RCM (701) preferably interfaces with the input of the edging conveyor (411). The type of mail and the associated throughput rate through this unit may be the same as from the unmodified DPRCS (400). The mail then exits the DPRCS (400), passes through the flats takeaway sorter (113) and enters into the loose mail processing system (109) as was accomplished in the prior art.

In order to minimize the floor space required for the RCM (701), the controls as well as the air handling system (1100) for the RCM (701) may be located in the area beneath the delayering conveyor (600). The size of the RCM (701) modification is preferably designed to be of generally the same length as the cull conveyor (406) and the waterfall assembly (408) of a traditional DPRCS (400), which it replaces or retrofits. Therefore, the RCM (701) modification preferably does not add significantly to the overall footprint of the DPRCS (400).

To provide a higher degree of safety, in an embodiment of the invention, the entire DPRCS (400) area, possibly including the hamper staging area, may be enclosed within a biological containment system or isolated environment to segregate the process from the other processes within the mail facility. This may be through a purposefully designed "clean room" type structure built into the postal facility, or may use a later added structure (such as, but not limited to, an inflatable structure) which is added after construction. In a still further embodiment, the modified DPRCS (400) may be mounted in a mobile structure such as a modified enclosed over-the-road truck trailer or a shipping container.

In embodiments, the RCM (701) may be provided as a replacement for the portion (700) of the DPRCS (400) allowing for these items to be removed and replaced. Alternatively, the RCM (701) could be provided as the components of a kit for use to convert an existing DPRCS (400) into the DPRCS (400) with an RCM (701). In a still further embodiment, the DPRCS could be originally manufactured with an RCM (701).

FIGS. 14 through 19 provide drawings of an embodiment of an RCM, air handling system, and DPRCS in accordance with the present invention. This embodiment is shown from multiple angles and multiple views showing structures similar to those described and shown in FIGS. 4–13.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A residue collection system for collecting residues from the mails, the system comprising:
    an aerosol chamber including:
        an outer shell defining an internal volume, said outer shell having an entrance port for allowing mail to enter said internal volume and an exit port for allowing mail to exit said internal volume, but otherwise substantially sealing said volume;
        a plurality of pinch roller arrays wherein a first pinch roller array and a second pinch roller array each comprises two sets of pinch rollers and where said first pinch roller array and a second pinch roller array are each capable of compressing a mail piece located within said internal volume; and
        an intake plenum, said intake plenum being capable of collecting air from said internal volume and being located between said first pinch roller array and a second pinch roller array which are adjacent each other;
    wherein said mail piece passes through said first pinch roller array, said first pinch roller array compressing said mail piece so as to force out some internal air from within said mail piece as said mail piece passes through;
    wherein said mail piece next passes through said second pinch roller array, said second pinch roller array also compressing said mail piece so as to force out additional air from within said mail piece as said mail piece passes through;
    wherein said airflow into said intake plenum is sufficient to maintain the portion of said internal volume between said first pinch roller array and said second pinch roller array at a negative pressure;
    wherein said additional air will include residue of a substance, when the substance is present in said mail piece;
    wherein said negative pressure is sufficient to maintain said residue within said internal volume;
    wherein said intake plenum takes in at least a portion of said additional air including said residue from said internal volume; and
    wherein said intake plenum can supply said additional air including said residue to a detection system capable of detecting said residue.

2. The residue collection system of claim 1 further comprising:
    a segregation component arranged prior to said aerosol chamber in a mail stream, said segregation component serving to provide said mail piece to said aerosol chamber.

3. The residue collection system of claim 2 wherein said segregation component includes a cull conveyor.

4. The residue collection system of claim 3 wherein said segregation component includes a delayering conveyor.

5. The residue collection system of claim 4 wherein said delayering conveyor is located after said cull conveyor.

6. The residue collection system of claim 5 wherein said delayering conveyor utilizes velocity differential separation relative to said cull conveyor.

7. The residue collection system of claim 5 wherein said delayering conveyor utilizes gravity separation.

8. The residue collection system of claim 2 wherein said segregation component includes a delayering conveyor.

9. The residue collection system of claim 8 wherein said delayering conveyor utilizes gravity separation.

10. The residue collection system of claim 1 wherein said residue is indicative of a Chemical or Biological Warfare Agent (CBWA) being present in said mail piece.

11. The residue collection system of claim 1 wherein said residue collection system is part of a Dual Pass Rough Cull System (DPRCS).

12. The residue collection system of claim 1 wherein each of said sets of pinch rollers comprises a plurality of disks.

13. The residue collection system of claim 12 wherein each of said sets of pinch rollers comprises a drive pinch roller and an idler pinch roller.

14. The residue collection system of claim 13 wherein, for each pinch roller set, at least one of said drive pinch roller and idler pinch roller is constructed of a flexible material.

15. The residue collection system of claim 14 wherein said flexible material is rubber.

16. The residue collection system of claim 12 wherein each disk of said plurality of disks has a width between 0.75 and 1.25 inches.

17. The residue collection system of claim 16 wherein said width is about 1 inch.

18. The residue collection system of claim 12 wherein said disks in said first pinch roller array are arranged farther apart than said disks in said second pinch roller array.

19. The residue collecting system of claim 18 wherein said mail piece passes through said first pinch roller array before passing through said second pinch roller array.

20. The residue collection system of claim 18 wherein said disks in said second pinch roller array are arranged touching each other.

21. The residue collection system of claim 1 wherein said air passes through a cyclonic separator system before reaching said detector.

22. The residue collection system of claim 1 wherein said mail piece is a letter.

23. The residue collection system of claim 1 wherein said mail piece is a flat.

24. A residue collection system comprising:
an aerosol chamber including:
an outer shell surrounding an internal volume, said outer shell having an entrance port for allowing mail to enter said internal volume and an exit port for allowing mail to exit said internal volume, but otherwise substantially sealing said volume;
at least two arrays of pinch rollers located within said internal volume, each of said arrays comprising two sets of pinch rollers, said at least two arrays arranged so that a first of said arrays of pinch rollers is nearer said entrance port and a second of said arrays is nearer said exit port;
an intake plenum, said intake plenum being capable of collecting air from said internal volume;
wherein the portion of said internal volume between said first of said arrays and said second of said arrays is maintained at a negative pressure;
wherein when a mail piece passes through said first array and said second array at least some air from within said mail piece is forced into said internal volume;
wherein at least some of said air from within said mail piece will include residue of a substance, when said substance is present in said mail piece; and
wherein said residue is pulled into said intake plenum.

25. A residue collection system comprising:
an aerosol chamber including:
an outer shell surrounding a first internal volume, said outer shell having an entrance port for allowing mail to enter said internal volume and an exit port for allowing mail to exit said internal volume, but otherwise substantially sealing said volume;
at least two arrays of pinch rollers located within said first internal volume, each of said arrays comprising two sets of pinch rollers; and
an intake plenum, said intake plenum being capable of collecting air from said first internal volume; and
a mail piece, said mail piece comprising a second internal volume which includes residue of a substance;
wherein, when said mail piece passes through said first array, some of said residue is ejected into said first internal volume;
wherein, when said mail piece passes through said second array, more of said residue is ejected into said first internal volume; and
wherein said first internal volume is maintained at a sufficient negative pressure that none of said ejected residue leaves said first internal volume.

26. A residue collection system comprising:
an aerosol chamber including:
an internal volume;
at least two arrays of pinch rollers located within said internal volume, each of said arrays comprising two sets of pinch rollers; and
an intake plenum, said intake plenum being capable of collecting air from said internal area and being located between a first array of said at least two arrays of pinch rollers and a second array of said at least two arrays of pinch rollers adjacent said first array; and
wherein a mail piece first passes through said first array and next passes through said second array;
wherein when said mail piece passes through said first array, said first array compresses said mail piece with a first pressure sufficient to force out some internal air from within said mail piece into said internal volume;
wherein when said mail piece passes through said second array, said second array compresses said mail piece with a second pressure sufficient to force out additional air from within said mail piece into said internal volume, said second pressure being greater than said first pressure;
wherein air within said internal volume includes residue of a substance, when the substance is present in said mail piece due to said residue being forced out of said mail piece with said internal air or said additional air;
wherein said intake plenum can take in at least a portion of said air including said residue from said internal area;
wherein said intake plenum can supply said air including said residue to a detection system capable of detecting said residue.

27. A residue collection system comprising:
an aerosol chamber including:
an internal volume;
at least two arrays of pinch rollers located within said internal volume, each of said arrays comprising two sets of pinch rollers, each of said sets of pinch rollers comprising a plurality of disks, said at least two arrays including a first array and a second array wherein said disks in each of said sets in said second array are arranged sufficiently close together as to touch; and
an intake plenum, said intake plenum being capable of collecting air from said internal area and being located between said first array and said second array;
wherein a mail piece first passes through said first array which compresses said mail piece with a first pressure sufficient to force out some internal air from within said mail piece into said internal volume;
wherein said mail piece second passes through said second array which compresses said mail piece with a second pressure sufficient to force out additional air from within said mail piece into said internal volume;
wherein air within said internal volume includes residue of a substance, when the substance is present in said mail piece due to said residue being forced out of said mail piece with said internal air or said additional air;
wherein said intake plenum can take in at least a portion of said air including said residue from said internal volume;
wherein said intake plenum can supply said air including said residue to a detection system capable of detecting said residue.

28. A residue collection system comprising:
an aerosol chamber including:
an internal volume;
at least two arrays of pinch rollers located within said internal volume, each of said arrays comprising two sets of pinch rollers, each of said sets of pinch rollers comprising a plurality of disks, said at least two arrays including a first array and a second array; and an intake plenum, said intake plenum being capable of collecting air from said internal volume and being located between said first array and said second array; and at least two mail pieces, each of said mail pieces having a different surface area;

wherein when a first of said at least two mail piece passes through said first array, a first number of said disks contacts said first of said at least two mail pieces with sufficient pressure to force out some internal air from within said first mail piece into said internal volume;

wherein when a second of said at least two mail pieces passes through said first array of said at least two arrays of pinch rollers, a second number of disks, different from said first number, contacts said second of said at least two mail pieces with sufficient pressure to force out some internal air from within said second mail piece into said internal volume;

wherein air within said internal volume includes residue of a substance, when said substance is present in one of said mail pieces, due to said residue being forced out of said mail piece and into said internal volume;

wherein said intake plenum can take in at least a portion of said air including said residue from said internal volume;

wherein said intake plenum can supply said air including said residue to a detection system capable of detecting said residue.

* * * * *